(12) United States Patent
Biris

(10) Patent No.: US 9,763,788 B2
(45) Date of Patent: Sep. 19, 2017

(54) BONE REGENERATION USING BIODEGRADABLE POLYMERIC NANOCOMPOSITE MATERIALS AND APPLICATIONS OF THE SAME

(71) Applicant: Board of Trustees of the University of Arkansas, Little Rock, AR (US)

(72) Inventor: Alexandru S. Biris, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 203 days.

(21) Appl. No.: 14/509,719

(22) Filed: Oct. 8, 2014

(65) Prior Publication Data
US 2015/0039097 A1 Feb. 5, 2015

Related U.S. Application Data

(63) Continuation-in-part of application No. 13/947,770, filed on Jul. 22, 2013, now Pat. No. 8,936,805, which is a continuation-in-part of application No. 11/519,316, filed on Sep. 11, 2006, now Pat. No. 8,518,123, application No. 14/509,719, which is a continuation-in-part of application No. 13/947,827, filed on Jul. 22, 2013, now abandoned.

(60) Provisional application No. 60/715,841, filed on Sep. 9, 2005, provisional application No. 60/726,383, filed on Oct. 13, 2005, provisional application No. 61/800,588, filed on Mar. 15, 2013, provisional application No. 61/800,588, filed on Mar. 15, 2013.

(51) Int. Cl.
| | |
|---|---|
| A61F 2/28 | (2006.01) |
| B32B 37/24 | (2006.01) |
| B32B 37/26 | (2006.01) |
| B32B 38/00 | (2006.01) |
| A61L 27/36 | (2006.01) |
| A61L 27/38 | (2006.01) |
| A61L 27/44 | (2006.01) |
| A61L 27/46 | (2006.01) |
| A61L 27/50 | (2006.01) |
| A61L 27/54 | (2006.01) |
| A61L 27/56 | (2006.01) |
| A61L 27/58 | (2006.01) |

(52) U.S. Cl.
CPC ............ *A61F 2/28* (2013.01); *A61L 27/3608* (2013.01); *A61L 27/38* (2013.01); *A61L 27/44* (2013.01); *A61L 27/46* (2013.01); *A61L 27/50* (2013.01); *A61L 27/54* (2013.01); *A61L 27/56* (2013.01); *A61L 27/58* (2013.01); *B32B 37/24* (2013.01); *B32B 37/26* (2013.01); *B32B 38/0004* (2013.01); *A61F 2002/2835* (2013.01); *A61L 2300/414* (2013.01); *A61L 2300/64* (2013.01); *A61L 2400/12* (2013.01); *A61L 2430/02* (2013.01); *B32B 2037/243* (2013.01); *B32B 2307/7163* (2013.01); *B32B 2317/00* (2013.01); *B32B 2323/04* (2013.01); *B32B 2333/04* (2013.01); *B32B 2375/00* (2013.01); *B32B 2386/00* (2013.01); *Y10T 156/1062* (2015.01); *Y10T 156/1074* (2015.01)

(58) Field of Classification Search
CPC . A61F 2/28; A61L 27/10; A61L 27/18; A61L 27/20; A61L 27/22; A61L 27/30; A61L 27/34; A61L 27/3608; A61L 27/38; A61L 27/3813; A61L 27/3817; A61L 27/3821; A61L 27/3826; A61L 27/3834; A61L 27/58
See application file for complete search history.

(56) References Cited

U.S. PATENT DOCUMENTS

| | | |
|---|---|---|
| 4,786,501 A | 11/1988 | Janski et al. |
| 4,814,182 A | 3/1989 | Graham et al. |
| 4,839,215 A | 6/1989 | Starling et al. |

(Continued)

FOREIGN PATENT DOCUMENTS

| | | |
|---|---|---|
| EP | 0933089 B1 | 9/1998 |
| EP | 1270025 B1 | 5/2006 |

(Continued)

OTHER PUBLICATIONS

International Search Report issued by the Republic of Korea (Korean Intellectual Property Office) dated Jan. 18, 2016 for Application No. PCT/US2015/054516.

(Continued)

*Primary Examiner* — Alma Pipic
(74) *Attorney, Agent, or Firm* — Tim Tingkang Xia, Esq.; Locke Lord LLP

(57) ABSTRACT

A biocompatible structure includes one or more base structures for regeneration of different tissues. Each base structure includes alternately stacked polymer layers and spacer layers. The polymer layer includes a polymer and tissue forming nanoparticles. The polymer includes polyurethane. The tissue forming nanoparticles includes hydroxypatites (HAP) nanoparticles, polymeric nanoparticles, or nanofibers. The spacer layer includes bone particles, polymeric nanoparticles, or nanofibers. The weight percentage of tissue forming nanoparticles to the polymer in the polymer layer in one base structure is different from that in the other base structures. A method of producing the biocompatible structure includes forming multiple base structures stacked together, coating the stacked multiple base structures, and plasma treating the coated structure.

14 Claims, 17 Drawing Sheets

(56) References Cited

U.S. PATENT DOCUMENTS

| | | | |
|---|---|---|---|
| 4,898,734 A | 2/1990 | Mathiowitz et al. |
| 5,084,051 A | 1/1992 | Tormala et al. |
| 5,766,247 A | 6/1998 | Aoki et al. |
| 6,013,591 A | 1/2000 | Ying et al. |
| 6,025,034 A | 2/2000 | Strutt et al. |
| 6,096,295 A | 8/2000 | Fuller |
| 6,110,482 A | 8/2000 | Khouri et al. |
| 6,129,928 A | 10/2000 | Sarangapani et al. |
| 6,165,486 A | 12/2000 | Marra et al. |
| 6,207,218 B1 | 3/2001 | Layrolle et al. |
| 6,261,322 B1 | 7/2001 | Despres, III et al. |
| 6,270,347 B1 | 8/2001 | Webster et al. |
| 6,319,712 B1 | 11/2001 | Meenen et al. |
| 6,323,146 B1 | 11/2001 | Pugh et al. |
| 6,398,815 B1 | 6/2002 | Pope et al. |
| 6,399,215 B1 | 6/2002 | Zhu et al. |
| 6,399,693 B1 | 6/2002 | Brennan et al. |
| 6,426,114 B1 | 7/2002 | Troczynski et al. |
| 6,541,022 B1 | 4/2003 | Murphy et al. |
| 6,585,992 B2 | 7/2003 | Pugh et al. |
| 6,610,095 B1 | 8/2003 | Pope et al. |
| 6,689,375 B1 | 2/2004 | Wahlig et al. |
| 6,706,273 B1 | 3/2004 | Roessler |
| 6,730,252 B1 | 5/2004 | Teoh et al. |
| 6,840,961 B2 | 1/2005 | Tofighi et al. |
| 6,852,330 B2 | 2/2005 | Bowman et al. |
| 6,887,272 B2 | 5/2005 | Shinomiya et al. |
| 6,899,873 B2 | 5/2005 | Ma et al. |
| 6,899,876 B2 | 5/2005 | Houston |
| 8,652,215 B2 | 2/2014 | Bellamkonda et al. |
| 8,747,467 B2 | 6/2014 | Mills et al. |
| 2001/0005797 A1 | 6/2001 | Barlow et al. |
| 2001/0008649 A1 | 7/2001 | Layrolle et al. |
| 2001/0053406 A1 | 12/2001 | Layrolle et al. |
| 2002/0016635 A1 | 2/2002 | Despres, III et al. |
| 2002/0042657 A1 | 4/2002 | Pugh et al. |
| 2002/0073894 A1 | 6/2002 | Genge et al. |
| 2002/0084194 A1 | 7/2002 | Redepenning |
| 2002/0115742 A1 | 8/2002 | Trieu et al. |
| 2003/0031698 A1 | 2/2003 | Roeder et al. |
| 2003/0077311 A1 | 4/2003 | Vyakarnam et al. |
| 2003/0077398 A1 | 4/2003 | Strutt et al. |
| 2003/0099630 A1 | 5/2003 | DiBenedetto et al. |
| 2003/0099762 A1 | 5/2003 | Zhang et al. |
| 2003/0113686 A1 | 6/2003 | Jia et al. |
| 2003/0143258 A1 | 7/2003 | Knaack et al. |
| 2003/0152606 A1 | 8/2003 | Gerber |
| 2003/0153965 A1 | 8/2003 | Supronowicz et al. |
| 2003/0165440 A1 | 9/2003 | Roth et al. |
| 2003/0170378 A1 | 9/2003 | Wen et al. |
| 2003/0171820 A1 | 9/2003 | Wilshaw et al. |
| 2003/0180344 A1 | 9/2003 | Wise et al. |
| 2003/0203038 A1 | 10/2003 | Vail |
| 2003/0219466 A1 | 11/2003 | Kumta et al. |
| 2003/0232071 A1 | 12/2003 | Gower et al. |
| 2004/0024081 A1 | 2/2004 | Trieu et al. |
| 2004/0082998 A1 | 4/2004 | Shinomiya et al. |
| 2004/0091547 A1 | 5/2004 | Ben-Nissan et al. |
| 2004/0126405 A1 | 7/2004 | Sahatjian et al. |
| 2004/0131562 A1 | 7/2004 | Gower et al. |
| 2004/0138758 A1 | 7/2004 | Evans et al. |
| 2004/0153165 A1 | 8/2004 | Li et al. |
| 2004/0161444 A1 | 8/2004 | Song et al. |
| 2004/0161996 A1 | 8/2004 | Ward et al. |
| 2004/0191200 A1 | 9/2004 | Lezer et al. |
| 2004/0210209 A1 | 10/2004 | Yeung et al. |
| 2004/0213977 A1 | 10/2004 | Ward et al. |
| 2004/0236432 A1 | 11/2004 | Hyon et al. |
| 2004/0247644 A1 | 12/2004 | Bratt et al. |
| 2004/0249006 A1 | 12/2004 | Gleason et al. |
| 2004/0249472 A1 | 12/2004 | Liu et al. |
| 2004/0250729 A1 | 12/2004 | Jang et al. |
| 2004/0253290 A1 | 12/2004 | Kim et al. |
| 2004/0254668 A1 | 12/2004 | Jang et al. |
| 2005/0008672 A1 | 1/2005 | Winterbottom et al. |
| 2005/0013973 A1 | 1/2005 | Richter et al. |
| 2005/0019365 A1 | 1/2005 | Frauchiger et al. |
| 2005/0031704 A1 | 2/2005 | Ahn |
| 2005/0042252 A1 | 2/2005 | Tanaka et al. |
| 2005/0053638 A1 | 3/2005 | Tanaka et al. |
| 2005/0079200 A1 | 4/2005 | Rathenow et al. |
| 2005/0216081 A1 | 9/2005 | Taylor |
| 2006/0008504 A1 | 1/2006 | Kerr et al. |
| 2006/0293760 A1 | 12/2006 | DeDeyne |
| 2007/0061015 A1 | 3/2007 | Jensen et al. |
| 2008/0131425 A1 | 6/2008 | Garcia et al. |
| 2010/0104652 A1 | 4/2010 | Biris et al. |
| 2010/0196432 A1 | 8/2010 | Feinberg et al. |
| 2013/0064863 A1 | 3/2013 | Biris et al. |
| 2013/0150943 A1* | 6/2013 | Zheng .................. A61F 2/915 623/1.2 |

FOREIGN PATENT DOCUMENTS

| | | |
|---|---|---|
| EP | 1273312 B1 | 9/2006 |
| JP | 61201019 A | 9/1986 |
| JP | 09308681 A | 12/1997 |
| JP | 11267193 A | 10/1999 |
| JP | 2002248119 A | 9/2002 |
| WO | 03088925 A2 | 10/2003 |
| WO | 2004011050 A1 | 2/2004 |
| WO | 2004047880 A1 | 6/2004 |
| WO | 2005086849 A2 | 9/2005 |
| WO | 2005123155 A2 | 12/2005 |
| WO | 2014143131 A1 | 9/2014 |

OTHER PUBLICATIONS

"OsteoGraf/LD—Synthetic, Radiopaque, Resorbable Bone," Dentsply Friadent CeraMed, www.ceramed.com/PEPGEN/OSTEOGF_LD_MAIN_PG.shtml, retrieved Aug. 5, 2006.

"A Complete Focus on Dental Bone Regeneration and Tissue," Dentsply Friadent CeraMed, www.ceramed.com/PRODUCTS/products_reg.shtml, retrieved Aug. 5, 2006.

"OsteoGraf/N—Predictable Increase of Bone Dimension,"Dentsply Friadent CeraMed, www.ceramed.com/PEPGEN/OSTEOGF_N_MAIN_PG.shtml, retrieved Aug. 5, 2006.

Noumbissi et al., "Clinical, Histologic, and Histomorphometric Evaluation of Mineralized Solvent-Dehydrated Bone Allograft (Puros) in Human Maxillary Sinus Grafts," J. of Oral Implantology, 31:2, 171-79, 2005.

Minichetti et al., "Human Histologic Analysis of Mineralized Bone Allograft (Puros) Placement Before Implant Surgery,"J. of Oral Implantology, XXX:2, 74-82,2004.

Levin, Barry P., "Clinical case presenting the use of Straumann Bone Ceramic for ridge preservation i n the mandible," Starget, pp. 17-18, Jan. 2006.

"Bone Replacement Grafts," J. Periodontal, Academy Report, 76:9, 1603-1605, 2005.

"OrthoBlast II: A Powerful Combination for Creating New Bone." Brochure. IsoTis OrthoBiologics, 2004.

Collard, David M., Recent Publications, available at http://www.chemistry.gatech.edu/faculty/Collard, pp. 1-3, accessed on Oct. 2, 2003.

Collard Group, PUblications, available at http;//web.chemistry.gatech.edu/~collard/more/index.html, pp. 1-5, accessed on Oct. 2, 2008.

European Patent Office (ISA/EP), "International Search Report" for PCT/US2006/035144, EP, Feb. 6, 2008.

"Bioactive and Biodegradable Nanocomposites and Hybrid Biomaterials for Bone Regeneration". Journal of Functional Biomaterials, Jun. 20, 2012, vol. 3, No. 2, pp. 432-463, Allo et al.

Korean Intellectual Property Office (ISA/KR), "International Search Report" for PCT/US2013/051520, KR, Nov. 19, 2013.

Korean Intellectual Property Office (ISA/KR), "Written Opinion" for PCT/US2013/051520, KR, Nov. 19, 2013.

Fu, SY; Feng XQ; Lauke, B: Mai, YW. "Effects of particle size, particle, matrix interface adhesion and particle loading on mechani-

(56) References Cited

OTHER PUBLICATIONS cal properties of particulate-polymer composites". Composties: Part B. 29 (2008) 933-961. Jan. 26, 2008.

* cited by examiner

BONE REGENERATION USING BIODEGRADABLE POLYMERIC NANOCOMPOSITE MATERIALS AND APPLICATIONS OF THE SAME

CROSS-REFERENCE TO RELATED PATENT APPLICATIONS

This application is a continuation-in-part of U.S. patent application Ser. No. 13/947,770, filed on Jul. 22, 2013, entitled "BONE REGENERATION USING BIODEGRADABLE POLYMERIC NANOCOMPOSITE MATERIALS AND APPLICATIONS OF THE SAME" by Alexandru S. Biris, which status is allowed, hereinafter the '770 application. The '770 application is a continuation-in-part of U.S. patent application Ser. No. 11/519,316, filed on Sep. 11, 2006, entitled "SYSTEM AND METHOD FOR TISSUE GENERATION AND BONE REGENERATION" by Alexandru S. Biris and Peder Jensen, now U.S. Pat. No. 8,518,123 and itself claims priority and the benefit of U.S. Provisional Application Ser. No. 60/715,841, filed on Sep. 9, 2005, and U.S. Provisional Application Ser. No. 60/726,383, filed on Oct. 13, 2005. The '770 application also claims priority and the benefit of U.S. Provisional Application Ser. No. 61/800,588, filed on Mar. 15, 2013, entitled "BONE REGENERATION USING BIODEGRADABLE POLYMERIC NANOCOMPOSITE MATERIALS AND APPLICATIONS OF THE SAME."

This application is also a continuation-in-part of U.S. patent application Ser. No. 13/947,827, filed on Jul. 22, 2013, entitled "BIODEGRADABLE POLYMERIC NANOCOMPOSITE MATERIALS AND APPLICATIONS OF THE SAME" by Alexandru S. Biris, which itself claims priority and the benefit of U.S. Provisional Application Ser. No. 61/800,588, filed on Mar. 15, 2013, entitled "BONE REGENERATION USING BIODEGRADABLE POLYMERIC NANOCOMPOSITE MATERIALS AND APPLICATIONS OF THE SAME."

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

STATEMENT OF FEDERALLY-SPONSORED RESEARCH

This disclosure was made with Government support under Grant No. W81XWH-10-2-0130 awarded by the U.S. Department of Defense. The Government has certain rights in the disclosure.

FIELD

The present disclosure relates generally to a biocompatible structure having one or more base structures for bone and tissue regeneration, and more particularly to a biodegradable and bioresorbable nanocomposite incorporating polymer, nanostructured hydroxyapatite and optionally other beneficial factors.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Skeletal deficiencies from trauma, tumors and bone diseases, or abnormal development frequently require surgical procedures to attempt to restore normal bone function. Although most of these treatments are successful, they all have problems and limitations.

Therefore, a heretofore unaddressed need exists in the art to address the aforementioned deficiencies and inadequacies.

SUMMARY

Certain aspects of the present disclosure are directed to an implant including two or more biocompatible structures. Each of the biocompatible structures is biodegradable and bioresorbable.

In one aspect, the present disclosure is directed to a method of producing a biocompatible structure for bone and tissue regeneration. The method includes:

forming multiple first polymer layers by: dissolving a first polymer in a first solvent to form a first solution; adding first tissue forming nanoparticles to the first solution to form a second solution, where a first weight percentage of the first tissue forming nanoparticles to the first polymer is about 0.01-95%; applying the second solution to a first surface to form a first polymer film on the first surface, where the first tissue forming nanoparticles are dispersed in the first polymer film; and dividing the first polymer film into the multiple first polymer layers;

forming multiple second polymer layers by: dissolving a second polymer in a second solvent to form a third solution; adding second tissue forming nanoparticles to the third solution to form a fourth solution, where a second weight percentage of the second tissue forming nanoparticles to the second polymer is greater than the first weight percentage; applying the fourth solution to a second surface to form a second polymer film on the second surface, where the second tissue forming nanoparticles are dispersed in the second polymer film; and dividing the second polymer film into the multiple second polymer layers; and forming the biocompatible structure by the first polymer layers, first spacer particles, the second polymer layers, second spacer particles, and a fifth solution.

In one embodiment, the formed biocompatible structure includes the first polymer layers, the second polymer layers, the first spacer particles placed between two of the first polymer layers, and the second spacer particles placed between two of the second polymer layers.

In one embodiment, the fifth solution includes at least one of the first and the second tissue forming particles, at least one of the first polymer and the second polymer, and at least one of the first solvent and the second solvent.

In one embodiment, the step of forming the multiple first polymer layers further includes: stirring the first solution to uniformly distribute the first polymer in the first solution; sonicating the second solution to uniformly distribute the first polymer and the first tissue forming nanoparticles in the second solution; and drying the second solution on the first surface to form the first polymer film on the first surface.

In one embodiment, the step of forming the multiple second polymer layers further includes: stirring the third solution to uniformly distribute the second polymer in the third solution; sonicating the fourth solution to uniformly distribute the second polymer and the second tissue forming nanoparticles in the fourth solution; and drying the fourth solution on the second surface to form the second polymer film on the second surface.

In one embodiment, the step of forming the biocompatible structure includes: constructing a first base structure by stacking the first polymer layers and first spacer layers alternatively, wherein each of the first spacer layers is formed by the first spacer particles; constructing a second base structure on the first base structure by stacking the second polymer layers and second spacer layers alternatively, wherein each of the second spacer layers is formed by the second spacer particles; applying the fifth solution to the first base structure and the second base structure to form a coated structure; and adding third spacer particles to the coated structure to form the biocompatible structure.

In one embodiment, after adding the third spacer particles to the coated structure, further including plasma treating the coated structure. The plasma treating may be a nitrogen or oxygen plasma treating.

In one embodiment, at least one of the first polymer layers, the second polymer layers, the first base structure, the second base structure, and the biocompatible structure is manufactured by 3D printing or layer by layer 2D printing.

In one embodiment, at least one of a thickness of the first polymer layer, a distance between two neighboring first polymer layers, a thickness of the first spacer layer, a porosity of the first spacer particles is different from a thickness of the second polymer layer, a distance between two neighboring second polymer layers, a thickness of the first spacer layer, a porosity of the second spacer particles, respectively, such that when being applied to an implant site, each of the first and the second base structure corresponds to a type of tissue in the implant site, and facilitates regeneration of the corresponding tissue.

In one embodiment, a degradation rate of the first base structure is slower than a degradation rage of the second base structure.

In one embodiment, each of the first and the second base structures has a size and shape conforming to a size and shape of corresponding tissue of an implant site.

In one embodiment, the first polymer is the same as the second polymer, the first tissue forming nanoparticles are different from the second tissue forming nanoparticles, the first solvent is the same as the second solvent, the first weight percentage is about 15-30%, and the second weight percentage is about 10-25%.

In one embodiment, the first polymer is the same as the second polymer, the first tissue forming nanoparticles are the same as the second tissue forming nanoparticles, the first solvent is the same as the second solvent, the first weight percentage is about 15-30%, and the second weight percentage is about 10-25%.

In one embodiment, the first weight percentage is about 17-23%, and the second weight percentage is about 15-20%.

In one embodiment, the first weight percentage is about 25%, and the second weight percentage is about 22%.

In one embodiment, each of the first and second polymer includes a synthetic biodegradable polymer, a biodegradable polymer derived from natural source, or a mixture thereof. The synthetic biodegradable polymer includes polyurethane, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, polyphosphazene, or a mixture thereof.

The biodegradable polymer derived from natural source includes modified polysaccharides, modified proteins, or a mixture thereof. Each of the first and second tissue forming nanoparticles includes nanoparticles of hydroxypatites, tricalcium phosphates, mixed calcium phosphates and calcium carbonate, bone particles of zenograft, bone particles of allografts, bone particles of autografts, bone particles of alloplastic grafts, polymeric nanoparticles, nanofibers, or a mixture thereof. The surface is a polytetrafluoroethylene (PTFE) surface. The second tissue forming particles includes nano-sized bone particles, micro-sized bone particles, or a mixture thereof.

In one embodiment, the method further includes adding a third tissue forming material to the biocompatible structure. The third tissue forming material includes a bioactive material, cells, or a mixture thereof. The bioactive material includes proteins, enzymes, growth factors, amino acids, bone morphogenic proteins, platelet derived growth factors, vascular endothelial growth factors, or a mixture thereof. The cells includes epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof. In one embodiment, the cells include stem cells, bone cells or the cells required for the particular tissue.

In one embodiment, at least one of the first polymer layers and the second polymer layers has a length of about 0.005-50 centimeter, a width of about 0.002-50 centimeter, and a thickness of about 0.001-500 millimeter, and each of the first base structure and the second base structure is in a cylindrical shape or a spherical shape.

In one aspect, the present disclosure is directed to a method of producing a biocompatible structure for bone and tissue regeneration. In certain embodiments, the biocompatible structure includes a first base structure, a second base structure, and a coating. Each of the first base structure and the second base structure includes a plurality of polymeric layers and a plurality of demineralized bone component particle layers. In one embodiment, the polymeric layers and the demineralized bone component particle layers are stacked alternately. The coating covers the first base structure and the second base structure. The method includes depositing each of the polymeric layers by air spray deposition, electrospray, droplet by droplet deposition, 2D printing, or 3D printing of a first solution comprising a polymer and a solvent, and depositing each of the demineralized bone component particle layers by electrostatic deposition or air spray of a second solution comprising demineralized bone component particles and the solvent.

In one aspect, the present disclosure is directed to a biocompatible structure. In one embodiment, the biocompatible structure includes a first base structure, a second base structure disposed on the first base structure, a coating surrounding the first base structure and the second base structure; and multiple third spacer particles attached to an outer surface of the coating.

In one embodiment, the first base structure includes multiple first polymer layers and multiple first spacer layers disposed between each of the two neighboring first polymer layers. The multiple first polymer layers are stacked to have a predetermined shape. Each of the first polymer layers is formed with a first polymer and first tissue forming nanoparticles. A first weight percentage of the first tissue forming nanoparticles to the first polymer layer is in a range of about 0.5-95%. Each of the first spacer layers includes first spacer particles.

In one embodiment, the second base structure includes multiple second polymer layers and multiple second spacer particle layers disposed between each of the two neighboring second polymer layers. The multiple second polymer layers are stacked to have a predetermined shape. Each of the second polymer layers is formed with a second polymer and a second tissue forming nanoparticles. A second weight percentage of the second tissue forming nanoparticles to the second polymer layer is in a range of about 0.5-95%. The first weight percentage is greater than the second weight percentage. Each of the second spacer layers includes second spacer particles.

In one embodiment, the first polymer is the same as the second polymer, the first tissue forming nanoparticles are HAP nanoparticles, the second tissue forming nanoparticles are nanofibers, the first weight percentage is about 15-30%, and the second weight percentage is about 10-25%.

In one embodiment, the first polymer is the same as the second polymer, the first tissue forming nanoparticles are the same as the second tissue forming nanoparticles, the first spacer particles and the second spacer particles are the same as the third spacer particles, the first weight percentage is about 15-30%, and the second weight percentage is about 10-25%.

In one embodiment, the first weight percentage is about 17-23%, the second weight percentage is about 15-20%.

In one embodiment, the first weight percentage is about 20%, the second weight percentage is about 18%.

In one embodiment, at least one of a thickness of the first polymer layer, a distance between two neighboring first polymer layers, a thickness of the first spacer layer, a porosity of the first spacer particles is different from a thickness of the second polymer layer, a distance between two neighboring second polymer layers, a thickness of the first spacer layer, a porosity of the second spacer particles, respectively, such that when being applied to an implant site, each of the first and the second base structure corresponds to a type of tissue in the implant site, and aids regeneration of the corresponding tissue.

In one embodiment, the distance between two neighboring first polymer layers is greater than the distance between two neighboring second polymer layers.

In one embodiment, the density of the first spacer particles in the first spacer layers is greater than the density of the second spacer particles in the second spacer layers.

In one embodiment, a degradation rate of the first base structure is slower than a degradation rage of the second base structure.

In one embodiment, each of the first base structure and the second base structure of the biocompatible structure has a size and shape conforming to a size and shape of the corresponding tissue of the implant site.

In one embodiment, each of the first polymer and the second polymer includes a synthetic biodegradable polymer, a biodegradable polymer derived from natural source, or a mixture thereof.

In one embodiment, the synthetic biodegradable polymer includes polyurethane, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, polyphosphazene, or a mixture thereof.

In one embodiment, the biodegradable polymer derived from natural source includes modified polysaccharides, modified proteins, or a mixture thereof;

In one embodiment, each of the first and second tissue forming nanoparticles includes nanoparticles of hydroxypatites (HAP), tricalcium phosphates, mixed calcium phosphates and calcium carbonate, bone particles of zenograft, bone particles of allografts, bone particles of autografts, bone particles of alloplastic grafts, polymeric nanoparticles, nanofibers, or a mixture thereof.

In one embodiment, each of the first spacer particles, the second spacer particles, and the third spacer particles includes nano-sized bone particles, micro-sized bone particles, polymeric nanoparticles, nanofibers, or a mixture thereof.

In one embodiment, the first spacer particles are bone particles, and the second spacer particles are polymeric nanoparticles or polymeric nanofibers.

In one embodiment, the biocompatible structure further includes a third tissue forming material.

In one embodiment, the third tissue forming material includes a bioactive material, cells, or a mixture thereof.

In one embodiment, the bioactive material includes proteins, enzymes, growth factors, amino acids, bone morphogenic proteins, platelet derived growth factors, vascular endothelial growth factors, or a mixture thereof.

In one embodiment, the cells includes epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof.

In one embodiment, at least one of the first and second polymer layers has a length of about 0.05-200 centimeter, a width of about 0.02-50 centimeter, and a thickness of about 0.01-500 millimeter, and each of the first and the second scaffold is in a cylindrical shape, rectangular shape or a spherical shape.

In one embodiment, the biocompatible structure of claim is plasma treated. The plasma treating may be a nitrogen or oxygen plasma treating.

Certain aspects of the present disclosure are directed to a method of treating bone deficiencies. The method includes applying an implant to an implant surgical site. The implant includes one or more biocompatible structures. The biocompatible structure includes polymer layers stacked to have a predetermined shape, bone particle layers disposed between each of the two neighboring polymer layers; a coating surrounding the polymer layers and bone particle layers; and bone particles attached to an outer surface of the coating. Each of the polymer layers is formed with a polymer and first tissue forming nanoparticles. The implant surgical site can have deficiencies of different tissues. The predetermined shape of each biocompatible structure in the implant is configured to conform to a corresponding tissue of the implant surgical site. A weight percentage of the first tissue forming nanoparticles to the polymer is about 5-50% such that a resorption rate of the biocompatible structure substantially matches a rate of tissue generation in the biocompatible structure.

BRIEF DESCRIPTION OF THE DRAWINGS

The accompanying drawings illustrate one or more embodiments of the disclosure and, together with the written description, serve to explain the principles of the disclosure. The same reference numbers may be used throughout the drawings to refer to the same or like elements in the embodiments.

DETAILED DESCRIPTION

Figure 1A:
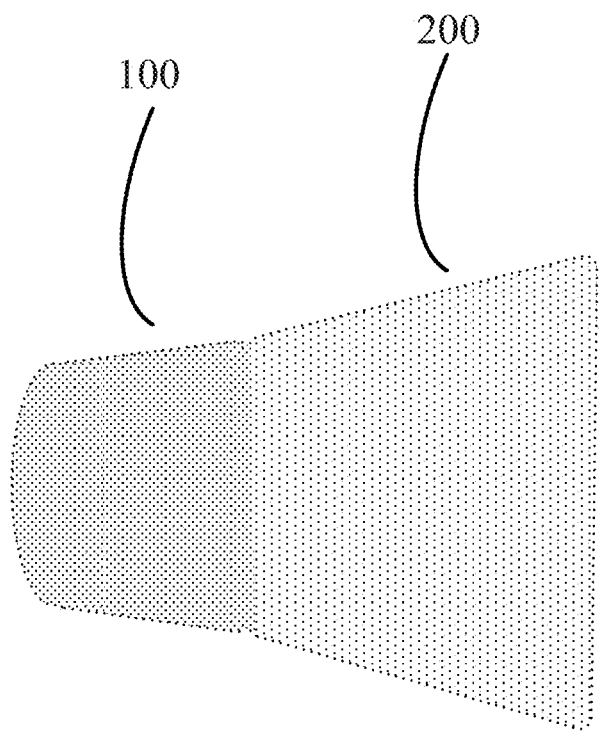
FIG. 1A illustrates a biocompatible structure according to certain embodiments of the present disclosure.

The disclosure will now be described more fully hereinafter with reference to the accompanying drawings, in which exemplary embodiments of the disclosure are shown. This invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the disclosure or of any exemplified term. Likewise, the disclosure is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the disclosure.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the disclosure.

Typically, terms such as "about," "approximately," "generally," "substantially," and the like unless otherwise indicated mean within 20 percent, preferably within 10 percent, preferably within 5 percent, and even more preferably within 3 percent of a given value or range. Numerical quantities given herein are approximate, meaning that the term "about," "approximately," "generally," or "substantially" can be inferred if not expressly stated.

Typically, "nanoscopic-scale," "nanoscopic," "nanometer-scale," "nanoscale," the "nano-" prefix, and the like refers to elements or articles having widths or diameters of less than about 1 μm, preferably less than about 100 nm in some cases. Specified widths can be smallest width (i.e. a width as specified where, at that location, the article can have a larger width in a different dimension), or largest width (i.e. where, at that location, the article's width is no wider than as specified, but can have a length that is greater), unless pointed out otherwise.

In most of the tissue trauma, there is loss of more than one type of tissues in an implant surgical site of a human or an animal. A biocompatible structure can be adapted to include multiple base structures having different properties, thus facilitating regeneration of two or more tissues in the implant surgical site of the human or the animal, or facilitating regeneration of tissues in a non-implant surgical site of the human or the animal and then transferred to the implant site, or facilitating regeneration of tissues in vitro or in the lab and then transferred to the implant surgical site. Alternatively, the biocompatible structure can have only one base structure.

FIG. 1A schematically shows structure of a biocompatible structure 90 according to certain embodiments of the present disclosure. In one embodiment as shown in FIG. 1A, the biocompatible structure 90 has two base structures. Alternatively, the biocompatible structure 90 can include various number of (such as three, four, five, and six, or more) base structures. In one embodiment, the implant surgical site may have a bone tissue loss and a muscle tissue loss. In certain embodiments, the biocompatible structure 90 has a first base structure 100 and a second base structure 200, which have different properties for facilitating regeneration of different tissues in the implant site. The first base structure 100 has specific polymer layer thickness, polymer layer distance, spacer particle layer thickness, spacer particle density, and degradation rate that allow bone regeneration in the bone loss portion of the implant surgical site. The second base structure 200 has specific polymer layer thickness, polymer layer distance, spacer particle layer thickness, spacer particle density, and degradation rate that allow muscle regeneration in the muscle tissue loss portion of the implant surgical site. The biocompatible structure 90 can be in any shape that conforms to a shape of the implant site. For example, each of the first base structure 100 and the second base structure 200 can have a cylindrical shape, a rectangular shape, or a spherical shape.

Figure 1B:
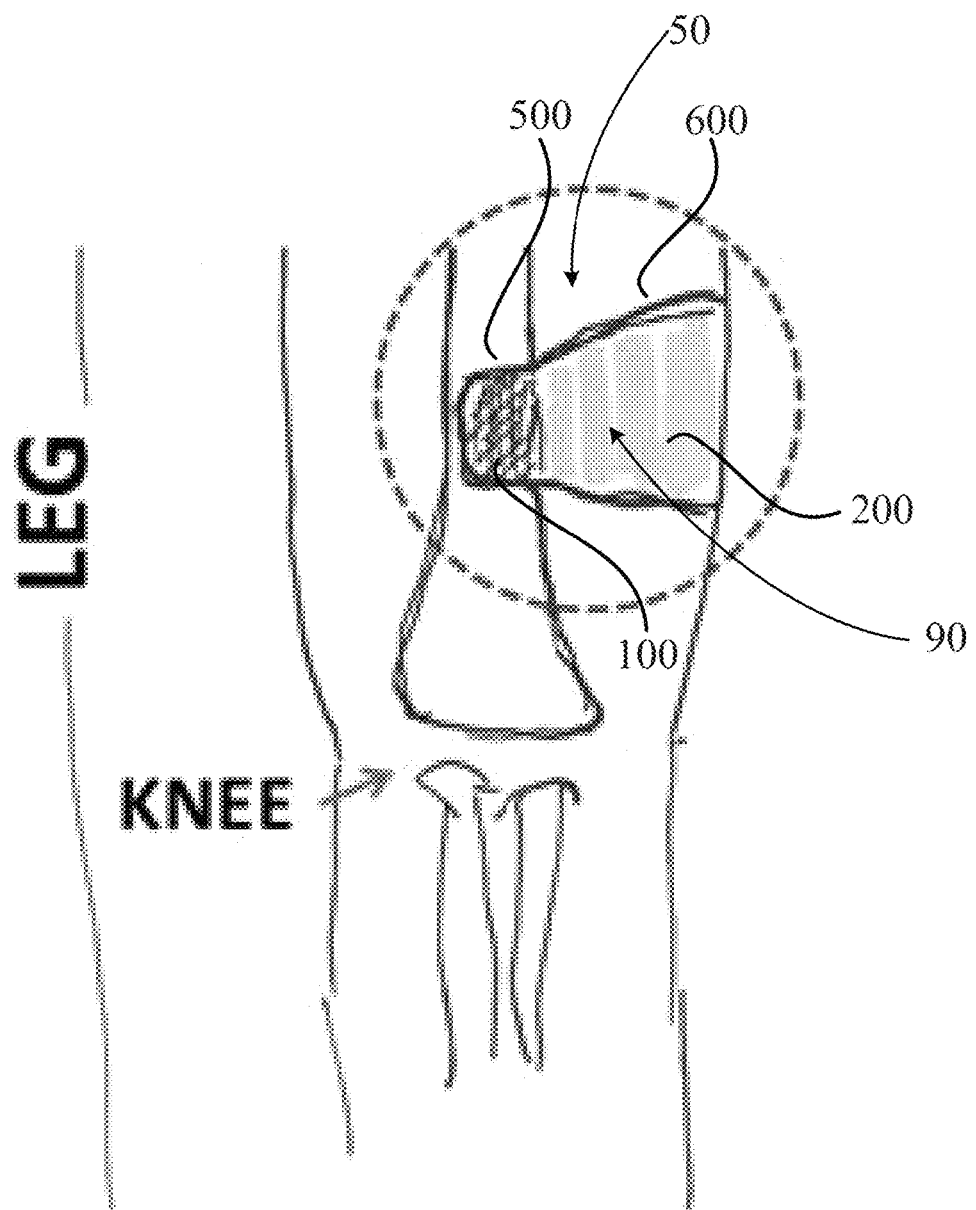
FIG. 1B illustrates a biocompatible structure inserted into an implant surgical site according to certain embodiments of the present disclosure.
Figure 1C:
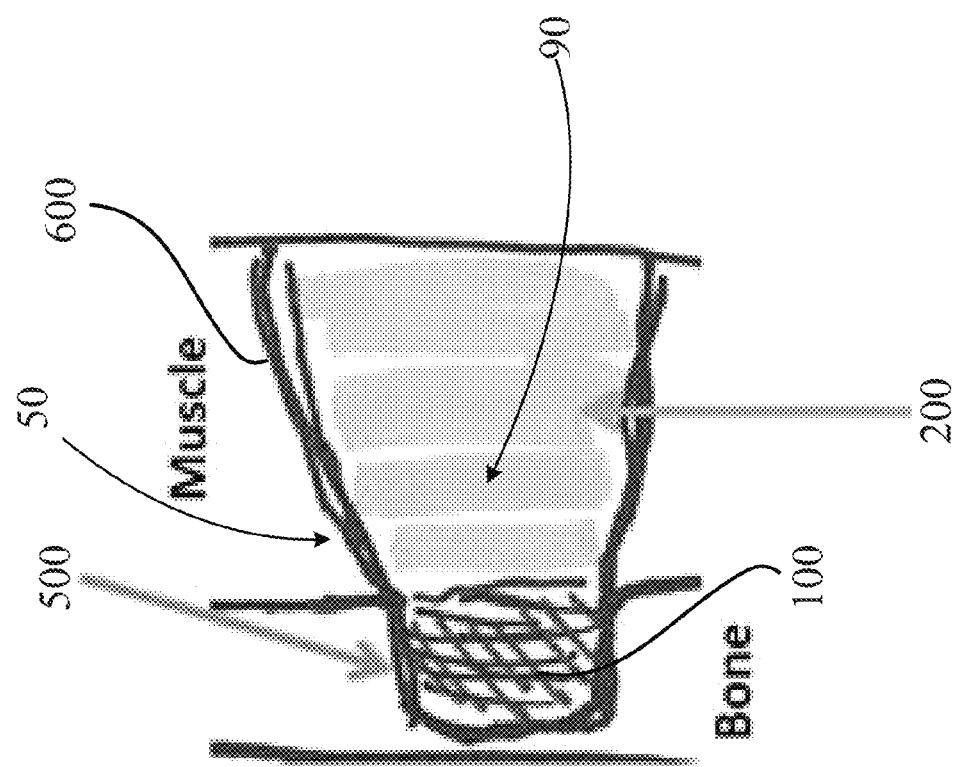
FIG. 1C illustrates an enlarged view of a part circled in FIG. 1B.

In certain embodiments, the base structures 100 and 200 in the biocompatible structure 90 have different properties, such as mechanical properties or biological properties, the mechanical properties can include intensity, pore density etc., and the different base structures correspond to different tissues in the implant surgical site. In certain embodiments, as shown in FIG. 1B and FIG. 1C, the implant surgical site 50 includes a bone area 500 and a muscle area 600. Correspondingly, the biocompatible structure 90 including the first base structure 100 and the second base structure 200 is applied to the implant surgical site 50. The size and the shape of the first base structure 100 correspond to the size and the shape of the bone area 500, and the properties of the first base structure 100 is suitable for the regeneration of bone tissue in the bone area 500. For example, the base 100 can be configured to meet the needs for the regeneration of bone tissue, can have mechanical properties matching the tissues to be regenerated, and can deliver growth factors specific for bone regeneration, cells, and/or can deliver antimicrobials. The size and the shape of the second base structure 200 correspond to the size and the shape of the muscle area 600, the properties of the second base structure 200 is suitable for the regeneration of muscle in the muscle area 600, and the second base structure 200 can carry cells and/or growth factors that are specific to this type of tissue regeneration. In other embodiments, the first base structure 100 and the second base structure 200 correspond to different portions of a bone loss, and are configured for the regeneration of the tissues in the different portions of the bone loss. The different portions of the bone loss have different properties, for example, one bone loss portion has a higher density than the other portion of the bone loss.

Figure 2A:
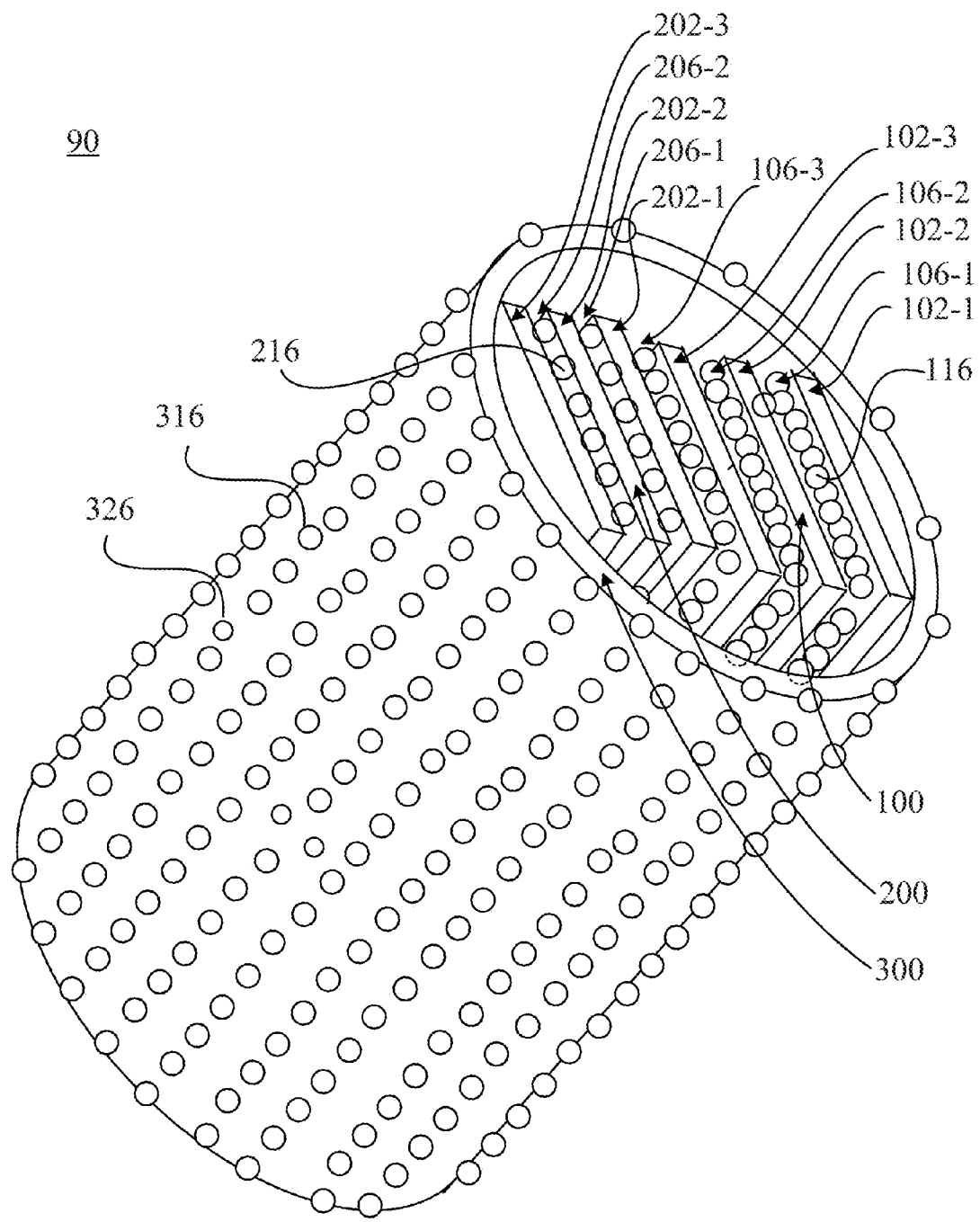
FIG. 2A illustrates a biocompatible structure having two base structures according to certain embodiments of the present disclosure.

FIG. 2A schematically shows a biocompatible structure 90 according to certain embodiments of the present disclosure. The biocompatible structure 90 can includes one or more base structures. In one embodiment, the biocompatible structure 90 includes a first base structure 100 and a second base structure 200. Each of the base structures can be in any shape that conforms to a shape or part of a shape of an implant site. For example, each of the base structures can have a cylindrical shape, a rectangular shape, or a spherical shape.

Figure 2B:
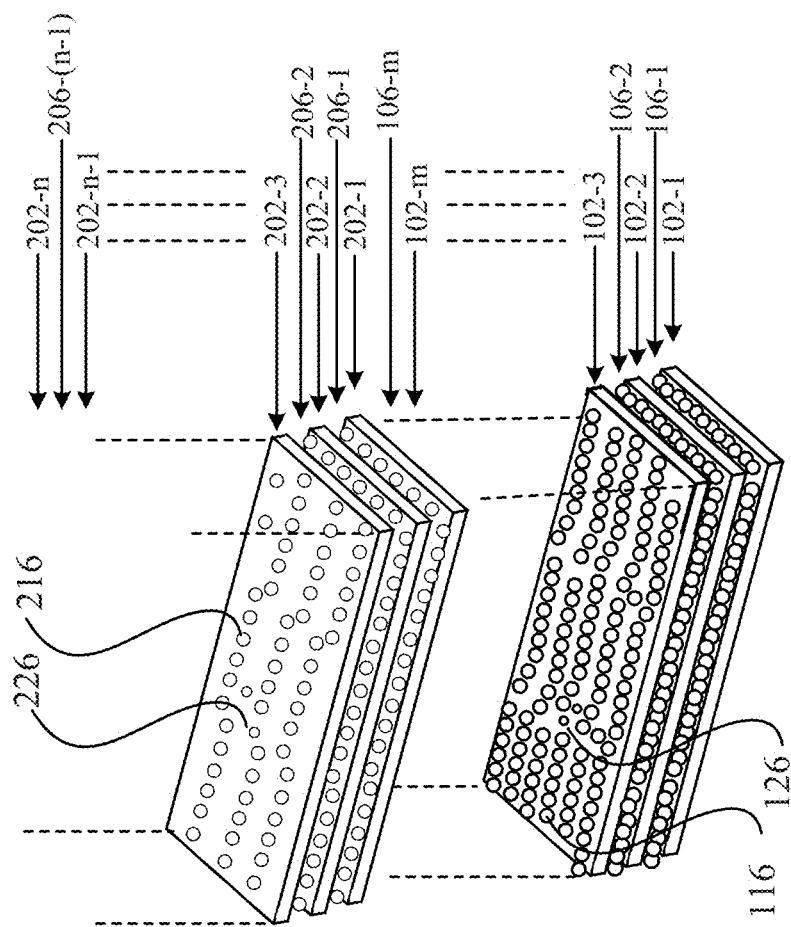
FIG. 2B illustrates base structures of the biocompatible structure according to certain embodiments of the present disclosure.
Figure 2C:
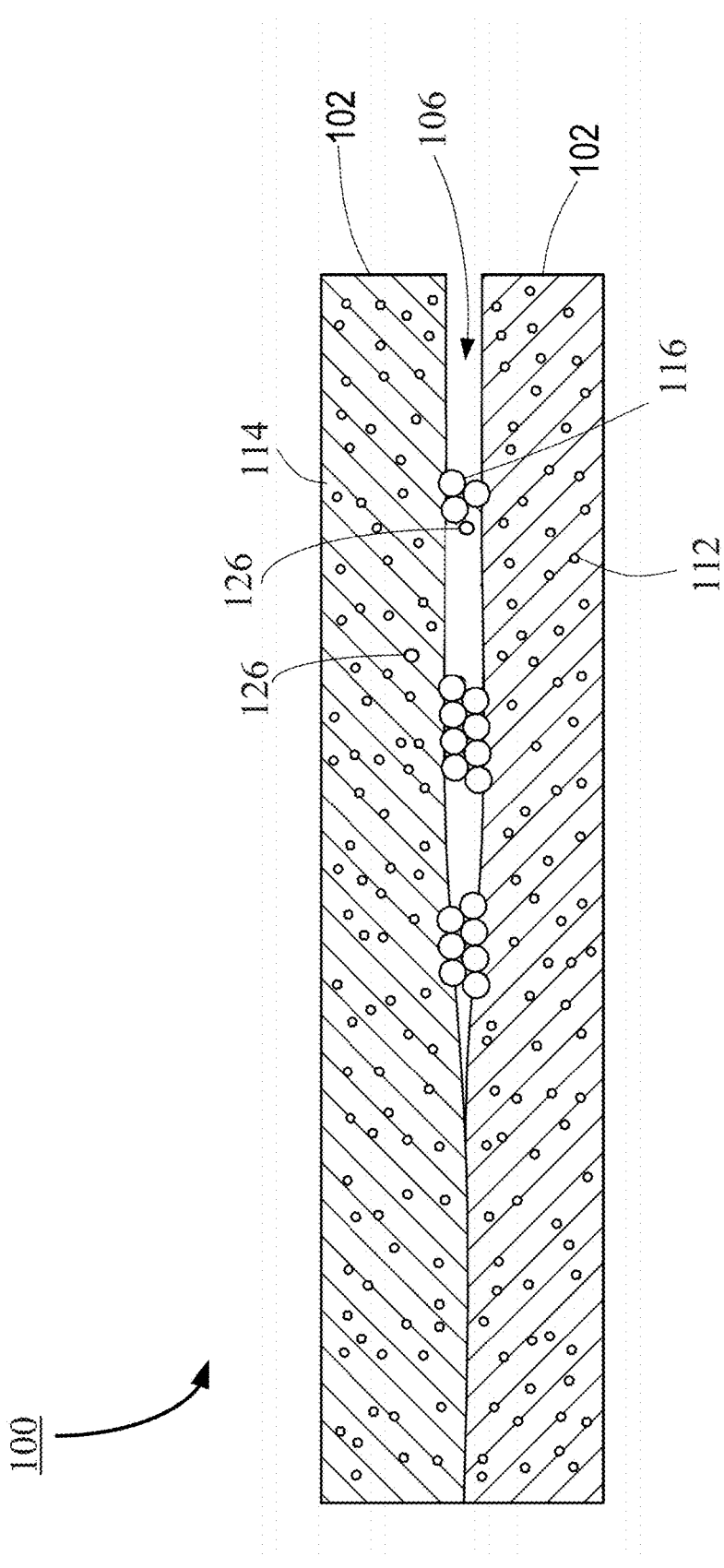
FIG. 2C illustrates a part of a base structure of the biocompatible structure according to certain embodiments of the present disclosure.

As shown in FIGS. 2A-2C, the biocompatible structure 90 includes the first base structure 100, the second base structure 200, and a coating 300 surrounding the first base structure 100 and the second base structure 200.

The first base structure 100 includes two or more first polymer layers 102 stacked together. Only three first polymer layers 102-1, 102-2, and 102-3 are shown in FIG. 2A. However, as shown in FIG. 2B, the number of the first polymer layers 102 can be m, where m is a positive integer. In certain embodiments, the first base structure 100 includes the first polymer layer 102-1, the first spacer layer 106-1, the first polymer layer 102-2, the first spacer layer 106-2, the first polymer layer 102-3, the second spacer layer 106-3 . . . the first spacer layer 106-(m-1), the first polymer layer 102-m, and optionally the first spacer layer 106-m stacked layer by layer. As will be described below, the first polymer layers 102 each have first tissue forming nanoparticles 112 dispersed in a first polymer matrix 114. In certain embodiments, the size of the first tissue forming nanoparticles 112 is about 0.1 nm to 1000 nm. In certain embodiments, the size of the first tissue forming nanoparticles 112 is about 1 nm to 500 nm. In certain embodiments, the size of the first tissue forming nanoparticles 112 is about 2-300 nm. In certain embodiments, the size of the first tissue forming nanoparticles 112 is about 50-150 nm. In certain embodiments, the first tissue forming nanoparticles 112 are hydroxypatite (HAP) nanoparticles. In certain embodiments, the thickness of the first polymer layers 102 is about 0.001 mm-100 mm. In certain embodiments, the thickness of the first polymer layers 102 is about 0.01 mm-50 mm. In certain embodiments, the thickness of the first polymer layers 102 is about 0.1 mm-20 mm. In certain embodiments, the thickness of the first polymer layers 102 is about 1 mm-3 mm. In certain embodiments, the first polymer layers 102 can be made as strips. In certain embodiments, the first polymer layers 102 each can have a length of 0.005-50 cm, a width of 0.002-50 cm, and a thickness of 0.001-50 mm. In certain embodiments, the first polymer layers 102 each can have a length of 0.05-10 cm, a width of 0.02-5 cm, and a thickness of 0.01-5 mm. In certain embodiments, the first polymer layers 102 each can have a length of 0.5-5 cm, a width of 0.2-3 cm, and a thickness of 0.1-3 mm. In certain embodiments, the first polymer layers 102 each can have a length of about 1-3 cm, a width of about 0.5-2 cm, and a thickness of about 0.5-2 mm. Further, first spacer particles 116 are located in between any two of the first polymer layers 102 and can function as a first spacer layer 106 between the first polymer layers 102. In certain embodiments, the first spacer particles 116 each have a diameter of about 2-100 μm. In certain embodiments, the first spacer particles 116 each have a diameter of about 0.5-1000 μm. In certain embodiments, the first spacer particles 116 each have a diameter of about 2-100 μm. In certain embodiments, the first spacer particles 116 each have a diameter of about 10-50 μm. In certain embodiments, the first spacer particles 116 are partially embedded, or trapped, in the surface portion of the first polymer layers 102. In certain embodiments, each first spacer layer 106 can have a thickness between approximately 0.001 mm and approximately 50 mm. In certain embodiments, the thickness of the first spacer layers 106 is about 0.001 mm-100 mm. In certain embodiments, the thickness of the first spacer layers 106 is about 0.01 mm-50 mm. In certain embodiments, the thickness of the first spacer layers 106 is about 0.1 mm-20 mm. In certain embodiments, the thickness of the first spacer layers 106 is about 1 mm-3 mm. In certain embodiments, each first spacer layer 106 can have a thickness between approximately 0.001 mm and approximately 50 mm, but are typically less than 3 mm. The layers can be stacked in vitro, in vivo, or in situ on top of one another. In certain embodiments, the first spacer particles 116 can be bone particles or composite particulates as described below. In certain embodiments, the first spacer particles 116 can be HAP particles as described below. In certain embodiments, a portion of one first polymer layer 102 can contact a portion of an adjacent first polymer layer 102. In certain embodiments, those contacted portions can cross-link with each other. In certain embodiments, the base 100, is covered or contains a surface film formed of a hydrophilic polymeric structure that has a high capacity for liquid absorption such that immediately upon insertion, the scaffold increases slightly in size and locks itself in the bone defect.

The second base structure 200 includes two or more second polymer layers 202 stacked together. Only three second polymer layers 202-1, 202-2, and 202-3 are shown in FIG. 2A. However, as shown in FIG. 2B, the number of the second polymer layers 202 can be n, where n is a positive integer. The integers m and n can be the same value or different value, according to the size and thickness needed for the first base structure 100 and the second base structure 200. In certain embodiments, the second base structure 200 includes the second polymer layer 202-1, the second spacer layer 206-1, the second polymer layer 202-2, the second spacer layer 206-2, the second polymer layer 202-3, the second spacer layer 206-3 . . . the second spacer layer 206-(n-1), the second polymer layer 202-n, and optionally the second spacer layer 206-n stacked layer by layer on the first base structure 100. In certain embodiments, the first base structure and the second base structure is separated by a first spacer layer 106 or a second spacer layer 206. In certain embodiments, the first base structure and the second base structure has a first polymer layer 102-second spacer layer 206 interface. In certain embodiments, the first base structure and the second base structure has a first polymer layer 102-second polymer layer 202 interface. In certain embodiments, the first base structure and the second base structure has a first spacer layer 106-second polymer layer 202 interface. In certain embodiments, the first base structure and the second base structure has a first spacer layer 106-second spacer layer 206 interface.

As will be described below, the second polymer layers 202 each have second tissue forming nanoparticles 212 dispersed in a second polymer matrix 214. In certain embodiments, the size of the second tissue forming nanoparticles 212 is about 0.1 nm to 1000 nm. In certain embodiments, the size of the second tissue forming nanoparticles 212 is about 1 nm to 500 nm. In certain embodiments, the size of the second tissue forming nanoparticles 212 is about 2-300 nm. In certain embodiments, the size of the second tissue forming nanoparticles 112 is about 50-150 nm. The size of the second tissue forming nanoparticles 212 can be the same as or different from the first tissue forming nanoparticles 112. In certain embodiments, the first base structure 100 and the second base structure 200 are configured for regeneration of different bone portions, and the second tissue forming nanoparticles 212 are hydroxyapatite (HAP) nanoparticles. In certain embodiments, the first base structure and the second base structure 200 are configured for regeneration of bone loss and muscle tissue loss of an implant site respectively, and the second tissue forming nanoparticles 212 are polymeric nanoparticles or nanofibers. In certain embodiment, the HAP nanoparticle is not suitable as the second tissue forming nanoparticle 212 when the second base structure 200 is configured for the regeneration of muscle tissue. In certain embodiments, the second polymer layers 202 can be made as strips. In certain embodiments, the second polymer layers 202 each can have a length of 0.005-50 cm, a width of 0.002-50 cm, and a thickness of 0.001-50 mm. In certain embodiments, the second polymer layers 202 each can have a length of 0.05-10 cm, a width of 0.02-5 cm, and a thickness of 0.01-5 mm. In certain embodiments, the second polymer layers 202 each can have a length of 0.5-5 cm, a width of 0.2-3 cm, and a thickness of 0.1-3 mm. In certain embodiments, the second polymer layers 202 each can have a length of about 1-3 cm, a width of about 0.5-2 cm, and a thickness of about 0.5-2 mm.

Further, second spacer particles 216 are located in between any two of the second polymer layers 202 and can function as a second spacer layer 206 between the second polymer layers 202. In certain embodiments, the second spacer particles 216 each have a diameter of about 0.002-100 µm. In certain embodiments, the second spacer particles 216 each have a diameter of about 0.002-1000 µm. In certain embodiments, the second spacer particles 216 each have a diameter of about 0.002-100 µm. In certain embodiments, the second spacer particles 216 each have a diameter of about 10-50 µm. In certain embodiment, the second spacer particles 216 can be the same as or different from the first spacer particles 116. In certain embodiments, the second spacer particles 216 are partially embedded, or trapped, in the surface portion of the second polymer layers 202. In certain embodiment, the second spacer particles 206 are polymeric nanoparticles or polymeric nanofibers. The second polymeric nanoparticles 216 or the second polymeric nanofibers 206 can be deposited on the second polymer layer 202 by electrospray, air spray, or any other method that can deposit polymeric nanoparticles or nanofibers. In certain embodiments, each second spacer layer 206 can have a thickness between approximately 0.001 mm and approximately 50 mm. In certain embodiments, the thickness of the second spacer layers 206 is about 0.001 mm-100 mm. In certain embodiments, the thickness of the second spacer layers 206 is about 0.01 mm-50 mm. In certain embodiments, the thickness of the second spacer layers 206 is about 0.1 mm-20 mm. In certain embodiments, the thickness of the second spacer layers 206 is about 1 mm-3 mm. In certain embodiments, each second spacer layer 206 can have a thickness between approximately 0.001 mm and approximately 50 mm, but are typically less than 3 mm. In certain embodiment, the second spacer layers 206 can have a thickness the same as or different from the thickness of the first spacer layers 106. The layers can be stacked in vitro, in vivo, or in situ on top of one another. In certain embodiments, the second spacer particles 216 can be bone particles or composite particulates as described below. In certain embodiment, when the second base structure 200 is configured for muscle regeneration, the second spacer particles 216 are polymeric nanoparticles that are not HAP nanoparticles, or the second spacer particles 216 are polymeric nanofibers. In certain embodiments, a portion of one second polymer layer 202 can contact a portion of an adjacent second polymer layer 202. In certain embodiments, those contacted portions can cross-link with each other.

In certain embodiments, the first base structure 100 and the second base structure 200 have different properties. In certain embodiments, the first tissue forming nanoparticles 112 and the second tissue forming nanoparticles 212 are the same material, the first polymer matrix 114 and the second polymer matrix 214 are the same material, and the first space particles 116 and the second space particles 216 are the same material. Alternatively, in certain embodiments, the first polymer matrix 114 and the second polymer matrix 214 are the same material, but the first tissue forming nanoparticles 112 and the second tissue forming nanoparticles 212 are different material, and the first space particles 116 and the second space particles 216 are different material.

In certain embodiments, both the first tissue forming nanoparticles 112 and the second tissue forming nanoparticles are HAP nanoparticles, and the weight percentages of HAP nanoparticles in the polymer film of the first base structure 100 and the second base structure 200 are different. In one embodiment, the weight percentage of HAP nanoparticles in the first polymer film 102 is greater than the weight percentage of HAP nanoparticles in the second polymer film 202. In certain embodiments, the distances between the polymer layers of the first base structure 100 and the second base structure 200 are different. In one embodiment, the distance between the first polymer layers 102 in the first base structure 100 is less than the distance between the second polymer layers 202 in the second base structure 200. In certain embodiments, at least one of the size, shape, density, and porosity of the first spacer particles 116 in the first base structure 100 is different from that of the second spacer particles 216 in the second base structure 200. In certain embodiments, the density of the first spacer layer 106 is higher than the density of the second spacer layer in 206. In certain embodiment, the density of a layer is the weight (for example, in grams) per volume (for example, in cubic millimeters). Alternatively, the density of a layer can be the number of particles (for example, number of nanoparticles) per volume (for example, in cubic millimeters). In certain embodiments, the thickness of the first spacer layer 106 in the first base structure 100 is different from the thickness of the second spacer layer 206 in the second base structure 200. In certain embodiments, the thickness of the first spacer layer 106 in the first base structure 100 is greater than the thickness of the second spacer layer 206 in the second base structure 200. In certain embodiments, the first base structure 100 and the second base structure 200 of the biocompatible structure can have different degradation rates. In certain embodiments, the degradation rate of the first base structure 100 is slower than the degradation rate of the second base structure 200.

In certain embodiments, the first tissue forming nanoparticles 112 are HAP nanoparticles and the second tissue forming nanoparticles 212 are polymeric nanoparticles or nanofibers, and the weight percentages of HAP nanoparticles in the polymer film of the first base structure 100 and the weight percentage of polymeric nanoparticles or nanofibers in the second base structure 200 are different. In one embodiment, the weight percentage of HAP nanoparticles in the first polymer film 102 is greater than the weight percentage of polymeric nanoparticles or nanofibers in the second polymer film 202. In certain embodiments, the distances between the polymer layers of the first base structure 100 and the second base structure 200 are different. In one embodiment, the distance between the first polymer layers 102 in the first base structure 100 is less than the distance between the second polymer layers 202 in the second base structure 200. In certain embodiments, at least one of the size, shape, density, and porosity of the first spacer particles 116 in the first base structure 100 is different from that of the second spacer particles 216 in the second base structure 200. In certain embodiments, the density of the first spacer layer 106 is higher than the density of the second spacer layer in 206. In certain embodiment, the density of a layer is the weight per volume (for example, grams/cubic millimeters). Alternatively, the density of a layer can be the number of particles per volume (for example, number of nanoparticles/cubic millimeters or mole/cubic millimeter). In certain embodiments, the thickness of the first spacer layer 106 in the first base structure 100 is different from the thickness of the second spacer layer 206 in the second base structure 200. In certain embodiments, the thickness of the first spacer layer 106 in the first base structure 100 is greater than the thickness of the second spacer layer 206 in the second base structure 200. In certain embodiments, the first base structure 100 and the second base structure 200 of the biocompatible structure can have different degradation rates. In certain embodiments, the degradation rate of the first base structure 100 is slower than the degradation rate of the second base structure 200.

In certain embodiments, the biocompatible structure 90 includes a polymer coating 300 enclosing the stacked base structures 100 and 200. In certain embodiments, the surface of the coating 300 can have trapped third spacer particles 316. In certain embodiments, the third spacer particles 316 can form a layer and cover a substantial portion of the entire coating 300. The material of the third spacer particles 316 can be the same as the material of the first spacer particle 106 or the second spacer particle 206. In certain embodiments, the third spacer particles 316 each have a diameter of about 0.5-1000 μm. In certain embodiments, the third spacer particles 316 each have a diameter of about 2-100 μm. In certain embodiments, the third spacer particles 316 each have a diameter of about 10-50 μm. In certain embodiment, the third spacer particles 316 can be the same as or different from the first spacer particles 116 or the second spacer particles 216.

As discussed above, the first tissue forming nanoparticles 112 dispersed in the first polymer layer 102 or the second tissue forming nanoparticles 212 dispersed in the second polymer layer 202 are HAP nanoparticles and can have a dimensional range between 1-100 nanometer (nm). Hydroxylapatite, also called hydroxyapatite (HA or HAP), is a naturally occurring mineral form of calcium apatite with the formula $Ca_5(PO_4)_3(OH)$, but is usually written $Ca_{10}(PO_4)_6(OH)_2$ to denote that the crystal unit cell comprises two entities. Hydroxylapatite is the hydroxyl endmember of the complex apatite group. The $OH^-$ ion can be replaced by fluoride, chloride or carbonate, producing fluorapatite or chlorapatite. It crystallizes in the hexagonal crystal system. Pure hydroxylapatite powder is white. Naturally occurring apatites can, however, also have brown, yellow, or green colorations, comparable to the discolorations of dental fluorosis. Up to 50% of bone by weight is a modified form of hydroxylapatite (known as bone mineral). In certain embodiments, the HAP nanoparticles dispersed in the polymer layer can be composed of pure HAP, having significant crystallinity and very good dispensability due to the presence of oxygen groups on the surface.

The presence of first HAP nanoparticles 112 in the first polymer film 114, among other things, contributes to the pore size and the strength of the first polymer film 114. In addition, the concentration of first HAP nanoparticles 112 is also related to the degradation rate of the first polymer film 114 when the first polymer film 114 is used as implant material. The presence of second HAP nanoparticles 212 in the second polymer film 214, among other things, contributes to the pore size and the strength of the second polymer film 214. In addition, the concentration of second HAP nanoparticles 212 is also related to the degradation rate of the second polymer film 214 when the second polymer film is used as implant material.

In certain embodiments, the first HAP nanoparticles 112 can enhance bone/mineralization in bone cells. The first HAP nanoparticles 112, together with other nanomaterials, have the ability to increase the osteogenesis and mineralization in bone cells. In certain embodiments, the second HAP nanoparticles 212, together with other nanomaterials, have the ability to increase the growth of muscle cells.

In other embodiments, the first tissue forming nanoparticles 112 dispersed in the first polymer layer 102 are HAP nanoparticles and the second tissue forming nanoparticles 212 dispersed in the second polymer layer 202 are polymeric nanoparticles or nanofibers. The HAP nanoparticles 112 and the nanofibers 212 can have a dimensional range between 1-100 nanometer (nm).

The presence of first HAP nanoparticles 112 in the first polymer film 114, among other things, contributes to the pore size and the strength of the first polymer film 114. In addition, the concentration of first HAP nanoparticles 112 is also related to the degradation rate of the first polymer film 114 when the first polymer film 114 is used as implant material. The presence of nanofibers of polymeric nanoparticles 212 in the second polymer film 214, among other things, contributes to the pore size and the strength of the second polymer film 214. In addition, the concentration of the nanofibers of polymeric nanoparticles 212 is also related to the degradation rate of the second polymer film 214 when the second polymer film is used as implant material.

In certain embodiments, the first HAP nanoparticles 112 can enhance bone/mineralization in bone cells. The first HAP nanoparticles 112, together with other nanomaterials, have the ability to increase the osteogenesis and mineralization in bone cells. In certain embodiments, the nanofibers or polymeric nanoparticles 212, together with other nanomaterials, have the ability to increase the growth of muscle cells.

In certain embodiment, the first spacer particles 116 between the first polymer layers 102 or the second spacer particles 216 between the second polymer layers 202 of the present disclosure are bone particles, polymeric nanoparticles, or polymeric nanofibers. In certain embodiment, the bone particles can be autografts, allografts, xenografts (usually bovine) or alloplastic bone grafts (synthetic, such as tricalcium phosphate). In certain embodiment, the first and second bone particles 116 and 216 are treated with bone mineral products, or composite particles. Bones from slaughtered animals are an inexpensive raw material available in large quantities to produce bone mineral. Bones typically contain 50 to 60% of very fine crystallites of a form of modified hydroxylapatite, which is bonded by collagenic tissue and contains significant qualities of proteinaceous and other matter as well as associated fat and muscle tissues. Such a modified hydroxylapatite, in a pure state and has its essential crystal structure, represents a highly biocompatible remodeling bone implant material.

In certain embodiments, the first and second bone particles 116 and 216 include hydroxyapatite like crystallites with a particular degree of crystallinity, habit, and size (irregular platelike morphology, 5-10 nm in thickness 10-50 nm in length). The specific surface chemistry of the first and second bone particles 116 and 216 results from the calcium to phosphate ratio (37.5-38.0% calcium and 15.5-19.0% phosphorus). The inorganic phase of the first and second bone particles 116 and 216 contains porosity including ultrastructural interstices (10-100 nm) between the crystallites occurring naturally and produced by removal of the organic phase, and microscopic spaces (1-20 μm) including osteocyte lacunae, canaliculi, vascular channels, volkman's canals, and the canals of haversian systems (100-500 nm). The specific surface area, which is a measure of porosity is in the range 50 to 100 $m^2$/gram as determined by mercury porosimetry. The crystallinity of the first and second bone particles 116 and 216 can be characterized by X-ray diffraction and the porosity and crystallite morphology and size by electron microscopy.

In certain embodiment, the first and second bone particles 116 and 216 of the present disclosure are demineralized bone particles purchased from Geistlich BioOss, INC. The first and second bone particles 116 and 216 can be of bovine origin and treated such that only the inorganic structure is left, while the organic materials are removed. The first and second bone particles 116 and 216 are composed of powder particles with a diameter of 0.01-100 micrometer (μm).

In certain embodiments, the first and second spacer particles 116 and 216 can be large particles of HAP that, e.g., are produced in the lab, or composite particles (polymer and inorganic particles).

In certain embodiments, the spacers 216 can be polymer particles, polymer nanoparticles, or nanofibers with a diameter ranging from 2 nm to 100 microns. The length of the nanofibers can vary from 2 nm to a few centimeters and can be produced from the same polymer used for layer 202 or from a different polymer.

In certain embodiments, the first base structure 100 can include first bioactive materials 126. In certain embodiments, the first bioactive materials 126 can be sprayed on the surface of the first base structure 100, and/or incorporated in the first polymer structures 102 to promote bone growth.

In certain embodiments, the second base structure 200 can include second bioactive materials 226. In certain embodiments, the second bioactive materials 226 can be sprayed on the surface of the second base structure 200, and/or incorporated in the second polymer structures 202 to promote muscle growth.

The first and second bioactive materials 126 and 226 can be proteins/peptides, HA, drugs, growth factors, antibiotics (such as tetracycline, tobramycin, or others), and bone morphogenic proteins. Preferred first and second bioactive agents 126 and 226 are those that enhance tissue regeneration and/or tissue adhesion. Illustrative examples include growth factors, antibiotics, immuno-stimulators, and immuno-suppressants. In one embodiment, one of the first and second bioactive agents 126 and 226 may be a bone morphogenic protein such as bone morphogenetic proteins (BMP). In another embodiment, one of the second and the first bioactive agents 226 and 126 may be a growth factor such as fibroblast growth factors (FGF) or an agent which promotes the generation of connective tissue. In certain embodiments, the first bioactive agent 126 promotes regeneration of bone tissue and the second bioactive agent 226 promotes regeneration of muscle tissue.

In certain embodiments, tissue can also be grown in vivo by implanting the biocompatible structure 90 and stem cells or other types of suitable cells (liver cells for the growth of liver tissue; myocardial cells, muscle cells for replacing/restoring damaged heart tissue; epithelial cells, connective tissue cells for skin grafts; osteblasts for bone generation) to an implant site. Alternatively, tissue can be grown in vitro on the biocompatible structure 90 and then implanted (for example, for growth of connective tissue/coronary vessels for arterial grafts).

Suitable living cells can be placed in the biocompatible structure 90 before implantation or implanted together with the biocompatible structure 90 into a body. The living cells include epithelial cells (e.g., keratinocytes, adipocytes, hepatocytes), neurons, glial cells, astrocytes, podocytes, mammary epithelial cells, islet cells, endothelial cells (e.g., aortic, capillary and vein endothelial cells), and mesenchymal cells (e.g., dermal fibroblasts, mesothelial cells, osteoblasts), smooth muscle cells, striated muscle cells, ligament fibroblasts, tendon fibroblasts, chondrocytes, fibroblasts, and any of a variety of stem cells. Also suitable for use in the biocompatible structure 90 having one or more base structures are genetically modified cells, immunologically masked cells, and the like. Appropriate extracellular matrix proteins (ECM) may be added to the biocompatible structure to further promote cell ingrowth, tissue development, and cell differentiation within the scaffold. ECM proteins can include one or more of fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin.

Additional first and second bioactive agents 126 and 226 incorporated in the first base structure 100 and the second base structure 200, among other things, includes biologically active macromolecules helpful for cell growth, morphogenesis, differentiation, and tissue building, include growth factors, proteoglycans, glycosaminoglycans and polysaccharides. These compounds are believed to contain biological, physiological, and structural information for development or regeneration of tissue structure and function.

In certain embodiments, the biocompatible structure 90 having one or more base structures can be plasma-treated/activated/electro-sprayed to functionalize the surface of the biocompatible structure 10. Surface treatment can improve the hydrophilicity of the biocompatible structure 90 and promote the colonization of cells and the adhesion of bone particles to the surface and pores of the biocompatible structure 10. The surface can also be functionalized by electron or ion bombardment, laser irradiation and/or by any other physical or chemical surface reaction that affects the bonds near the surface. These processes can also help in sterilization of the implant. Plasma treatment breaks the surface bonds of the polymer. The plasma treatment may be a nitrogen or oxygen plasma treatment. In one example, after oxygen plasma treatment, oxygen atoms "attach" to the surface, changing the surface energy of the surface such that the surface becomes more hydrophilic and has oxygen and nitrogen rich functional groups.

The biocompatible structure 90 having the one or more base structures of the present disclosure is highly porous (for example, high surface area, the presence of voids, cavities, etc.), biocompatible, and allows for vascular ingrowth for bone/tissue regeneration. The surface typically does not inhibit any biological entity from interacting and to be hydrophilic or potentially become hydrophilic under different conditions or processes. Suitable materials for building structures for tissue/bone engineering and regeneration are certain polymers, ceramics, carbon-based materials and metals and metal composites. In certain embodiments, the first polymer layers 102 of the first base structure 100 or the second polymer layers 202 of the second base structure 200 of the present disclosure are formed from polyurethane. In certain embodiments, the biocompatible structure 90 has a layered structure composed of a polymeric material that may contain other substances, such as bioactive substances or substances promoting the generation of tissue growth. Those substances can be formed inside the first polymer layer 102 or on the surface of the polymer layer 102, and/or inside the second polymer layer 202 or on the surface of the second polymer layer 202. Some of the bioresorbable polymers may or may not require enzymes in order to degrade. The layered, porous design gives this structure a very high surface area for neovascularization and the growth of cells necessary for tissue regeneration. In addition, stem cells, osteoblasts, and other types of suitable cells can be incorporated into the system to aid in tissue generation. The biocompatible structure 90 can assume different shapes and dimensions as may be required for a particular application. The biocompatible structure 90 can be properly positioned in the surgical site directly or with medical pins, screws, or other devices.

The biocompatible structure 90 having one or more base structures is configured such that the degradation rate or the resorption rate of the biocompatible structure 90 is substantially matching a rate of tissue generation in the biocompatible structure 10. The controllable degradation rate of the biocompatible structure 90 can also provide controllable release of the bioactive substance or cells formed in the biocompatible structure 10. The polymer may have a different degradation rate than that of the biocompatible structure 10, but it contributes significantly to the degradation rate of the biocompatible structure 10. Accordingly, a polymer with suitable degradation property is chosen to produce the biocompatible structure 90 of the present disclosure. In certain embodiments, the first base structure 100 portion and the second base structure 200 portion of the biocompatible structure 200 have different degradation rates that corresponding respectively to the tissue type of the different part of the implant site.

The polymer layers 102 and 202 can be degraded by several mechanisms. The most common mechanism is diffusion. Further, the bioactive substances (agent) of the biocompatible structure can diffuse in various manners. The bioactive agent (drug) can have a core surrounded by an inert diffusion barrier, which can be membranes, capsules, microcapsules, liposomes, and hollow fibers. Alternatively, the active agent can be dispersed or dissolved in an inert polymer. Drug diffusion through the polymer matrix is the rate-limiting step, and release rates are determined by the choice of polymer and its consequent effect on the diffusion and partition coefficient of the drug to be released. By adjusting the diffusion method of the bioactive agent or cells, and components of the biocompatible structure component, suitable rate of bioactive agent or cells is achieved.

In certain embodiments, after implantation the biocompatible structure 90 can be eventually absorbed by the body, for example, by conversion of a material that is insoluble in water into one that is water/liquid-soluble, and thus need not be removed surgically.

In certain embodiments, the polymer layers 102 or 202 in the biocompatible structure 90 are biocompatible, processable, sterilizable, and capable of controlled stability or degradation in response to biological conditions. The reasons for designing a biocompatible structure 10 that degrades over time often go beyond the obvious desire to eliminate the need for retrieval. For example, the very strength of a rigid metallic implant used in bone fixation can lead to problems with "stress shielding," whereas a bioresorbable implant can increase ultimate bone strength by slowly transferring load to the bone as it heals. For drug delivery, the specific properties of various degradable systems can be precisely tailored to achieve optimal release kinetics of the drug or active agent.

An ideal biodegradable polymer layer 102 or 202 for medical applications typically has adequate mechanical properties to match the application (strong enough but not too strong), does not induce inflammation or other toxic response, may be fully metabolized once it degrades, and is sterilizable and easily processed into a final end product with an acceptable shelf life. In general, polymer degradation is accelerated by greater hydrophilicity in the backbone or end groups, greater reactivity among hydrolytic groups in the backbone, less crystallinity, greater porosity, and smaller finished device size.

A wide range of synthetic biodegradable polymers can be used to form the polymer matrix 102 or 202 of the present disclosure, including polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and polyphosphazene. There are also a number of biodegradable polymers derived from natural sources such as modified polysaccharides (cellulose, chitin, dextran) or modified proteins (fibrin, casein) that can be used to form the polymer matrix of the present disclosure.

Other materials can be tyrosine-derived polycarbonate poly(DTE-co-DT carbonate), in which the pendant group via the tyrosine—an amino acid—is either an ethyl ester (DTE) or free carboxylate (DT). Through alteration of the ratio of DTE to DT, the material's hydrophobic/hydrophilic balance and rate of in vivo degradation can be manipulated. It was shown that, as DT content increases, pore size decreases, the polymers become more hydrophilic and anionic, and cells attach more readily.

These materials are subject to both hydrolysis (via ester bonds) and oxidation (via ether bonds). Degradation rate is influenced by PEO molecular weight and content, and the copolymer with the highest water uptake degrades most rapidly.

These polymeric materials 102 and/or 202 can also be developed in such a way that they are stable in the biological environment, and degrade only under specific enzymatic conditions (plasmin, etc.). These materials can also include partially expressed fragments of human or animal fibrin such that the system degrades only in contact with plasmin.

The polymer 114 and/or 214 is preferably in solution mixed with a suitable solvent, and other substances can be added to the solution, for example, collagen, drugs, proteins, pep tides, hydroxyapetite crystals (HA), and antibiotics, depending on the type of tissue to be grown. The solution can be sonicated to promote mixing of the constituents.

By chosen a suitable polymer 114 and/or 214, the biocompatible structure 90 can achieve controllable supply of therapeutic, analgesic and/or antibacterial substances, growth factors, proteins, peptides, drugs, tissue subcomponents including but not limited to bone particles and hydroxyappetite, which promote growth, prevent infections and the like.

In certain embodiment, the biocompatible structure includes one or more base structures. The one or more base structures can have different properties. For example, for the biocompatible structure 90 having the first base structure 100 and the second base structure 200, the base structures 100 and 200 can have different properties as follows.

In certain embodiments, the weight percentage of the first tissue forming nanoparticles 112 in the first polymer film/layer 102 is defined as the total weight (e.g., grams) of the first tissue forming nanoparticles 112 divided by the total of the weight of the first tissue forming nanoparticles 112 (grams) and the weight of the solid first polymers 114 (grams) used for the preparation of the first polymer film 102. For example, a total of A grams of first nanoparticles 112 and a total of B grams of first polymers 114 are used to manufacture a first polymer film 102. The weight percentage of the first tissue forming nanoparticles 112 in the first polymer film 102 is calculated as $A/(A+B)$. In certain embodiments, the weight percentage of the first tissue forming nanoparticles 112 in the polymer layer 102 is about 0.05-95%. In certain embodiments, the weight percentage of the first tissue forming nanoparticles 112 in the polymer layer 102 is about 5-60%. In certain embodiments, the weight percentage of the first tissue forming nanoparticles 112 in the polymer layer 102 is about 10-30%. In certain embodiments, the weight percentage of the first tissue forming nanoparticles 112 in the polymer layer 102 is about 15-25%. In certain embodiments, the weight percentage of the tissue forming nanoparticles 112 in the polymer layer 102 is about 20%. In certain embodiment, the second polymer layer 202 can have similar features or different features as the first polymer layer 102. In certain embodiment, the weight percentage of the second tissue forming nanoparticles 212 in the polymer layer 202 is lower than that in the first polymer layer 102. In certain embodiment, the polymer layer 202 may not contain tissue forming nanoparticles 212. In certain embodiment, the weight percentage of tissue forming nanoparticles 212 in the polymer layer 202 is 0.1-50% lower than that in the first polymer layer 102. In certain embodiment, the weight percentage of tissue forming nanoparticles 212 in the polymer layer 202 is 1-5% lower than that in the first polymer layer 102. In certain embodiment, the weight percentage of tissue forming nanoparticles 212 in the polymer layer 202 is 2% lower than that in the first polymer layer 102

In certain embodiments, the first polymer matrix 114 of the first polymer layer 102 can be polyurethane. The first tissue forming nanoparticles 112 dispersed in the first polymer matrix 114 can be HAP nanoparticles. In certain embodiments, the second polymer matrix 214 of the second polymer layer 202 can be polyurethane. The second tissue forming nanoparticles 212 dispersed in the second polymer matrix 214 can be HAP nanoparticles, such that the first base structure 100 and the second base structure 200 are configured to regenerate different portions of a bone loss. In other embodiments, the second tissue forming nanoparticles 212 dispersed in the second polymer matrix 214 can be polymeric nanoparticle or nanofibers, such that the first base structure 100 and the second base structure 200 are configured to regenerate a bone loss and a muscle loss of an implant site respectively.

In certain embodiments, the first tissue forming nanoparticles 112 and the second tissue forming nanoparticles 212 are HAP nanoparticles, and the first polymer 114 and the second polymer 214 are the same polymer. The weight percentage of HAP nanoparticles in the polymer film is different in the first base structure 100 and the second base structure 200. In one embodiment, a first weight percentage of HAP nanoparticle in the first polymer layer 102 of the first base structure 100 is 10-30%, and a second weight percentage of HAP nanoparticle in the second polymer layer 202 of the second base structure 200 is 8-28%. In one embodiment, the first weight percentage is 15-25%, and the second weight percentage is 13-23%. In one embodiment, the first weight percentage is 18-22%, and the second weight percentage is 16-20%. In one embodiment, the first weight percentage is 20%, and the second weight percentage is 18%. In certain embodiments, the thickness of the first polymer layer 102 in the first base structure 100 is different from the thickness of the second polymer layer 202 in the second base structure 200.

In certain embodiments, the first tissue forming nanoparticles 112 are HAP nanoparticles, the second tissue forming nanoparticles 212 are nanofibers or polymeric nanoparticles, and the first polymer 114 and the second polymer 214 are the same polymer. The weight percentage of HAP nanoparticles in the first polymer film 102 is different from the nanofiber or polymeric nanoparticles in the second polymer film 202. In one embodiment, a first weight percentage of HAP nanoparticle in the first polymer layer 102 of the first base structure 100 is 10-30%, and a second weight percentage of nanofiber or polymeric nanoparticles in the second polymer layer 202 of the second base structure 200 is 8-28%. In one embodiment, the first weight percentage is 15-25%, and the second weight percentage is 13-23%. In one embodiment, the first weight percentage is 18-22%, and the second weight percentage is 16-20%. In one embodiment, the first weight percentage is 20%, and the second weight percentage is 18%. In certain embodiments, the thickness of the first polymer layer 102 in the first base structure 100 is different from the thickness of the second polymer layer 202 in the second base structure 200.

In certain embodiments, the size and shape of the first polymer layer 102 in the first base structure 100 are different from the size and shape of the second polymer layer 202 in the second base structure 200.

In certain embodiments, the thickness of the first polymer layer 102 and the second polymer layer 202 is about 0.001 mm-50 mm. In certain embodiments, the thickness of the first polymer layer 102 is different from the thickness of the second polymer layer 202. In certain embodiments, the thickness of the first polymer layer 102 is smaller than the thickness of the second polymer layer 202. In certain embodiments, the thickness of the first polymer layer 102 is about 0.1 mm-20 mm, and the thickness of the second polymer layer 202 is about 0.2 mm-30 mm. In certain embodiments, the thickness of the first polymer layer 102 is about 2 mm-5 mm, and the thickness of the second polymer layer 202 is about 3 mm-10 mm. In certain embodiments, the thickness of the first polymer layer 102 is about 3 mm, and the thickness of the second polymer layer 202 is about 5 mm.

In certain embodiments, the distances between the polymer layers in the first base structure 100 and the second base structure 200 are different. In certain embodiments, the distance between the first polymer layers 102 is greater than the distance between the second polymer layers 202. In certain embodiments, the distance between the first polymer layers 102 is about 0.002 mm-50 mm, and the distance between the second polymer layers 202 is about 0.001-40 mm. In certain embodiments, the distance between the first polymer layers 102 is about 0.02 mm-10 mm, and the thickness of the second spacer layer 206 is about 0.01 mm-8 mm. In certain embodiments, the distance between the first polymer layers 102 is about 0.2 mm-8 mm, and the distance between the second polymer layers 202 is about 0.1 mm-6 mm. In certain embodiments, the distance between the first polymer layers 102 about 1 mm-5 mm, and the distance between the second polymer layers 202 is about 0.5 mm-3 mm. In certain embodiments, the distance between the first polymer layers 102 is about 2 mm, and the distance between the second polymer layers 202 is about 1 mm.

In certain embodiments, the first spacer particles 116 in the first base structure 100 are different from the second spacer particle 216 in the second base structure 200. In certain embodiments, the size, shape, density, and porosity of the first spacer particles 116 are different from the size, shape, density, and porosity of the second spacer particles 216. In certain embodiments, the density of the first spacer layer 106 is higher than the density of the second spacer layer in 206. In certain embodiments, the porosity of the first spacer particles 116 is less than the porosity of the second spacer particles 216. In certain embodiments, the porosity of the first spacer particles 116 is about 50-90 m$^2$/gram, and the porosity of the second spacer particles 216 is about 60-100 m$^2$/gram. In certain embodiments, the porosity of the first spacer particles 116 is about 60-80 m$^2$/gram, and the porosity of the second spacer particles 216 is about 70-90 m$^2$/gram. In certain embodiments, the porosity of the first spacer particles 116 is about 70 m$^2$/gram, and the porosity of the second spacer particles 216 is about 80 m$^2$/gram. In certain embodiment, the first spacer particles 216 are bone particles or bone nanoparticles, and the second spacer particles 226 are polymeric nanoparticles or polymer nanofibers.

In certain embodiments, the thickness of the first spacer layer 106 in the first base structure 100 is different from the thickness of the second spacer layer 206 in the second base structure 200. In certain embodiment, the thickness of the first spacer layer 106 is greater than the thickness of the second spacer layer 206. In certain embodiments, the thickness of the first spacer layer 106 is about 0.002 mm-50 mm, and the thickness of the second spacer layer 206 is about 0.001 mm-40 mm. In certain embodiments, the thickness of the first spacer layer is about 0.02 mm-10 mm, and the thickness of the second spacer layer 206 is about 0.01 mm-8 mm. In certain embodiments, the thickness of the first spacer layer 106 is about 0.2 mm-8 mm, and the thickness of the second spacer layer 206 is about 0.1 mm-6 mm. In certain embodiments, the thickness of the first spacer layer 106 is about 1 mm-5 mm, and the thickness of the second spacer layer 206 is about 0.5 mm-3 mm. In certain embodiments, the thickness of the first spacer layer 106 is about 2 mm, and the thickness of the second spacer layer 206 is about 1 mm.

In certain embodiments, the density of the first spacer layer 106 in the first base structure 100 is different from the density of the second spacer layer 206 in the second base structure 200. In one embodiment, the density of the first spacer layer 106 is higher than the density of the second spacer layer in 206.

In certain embodiments, the first base structure 100 and the second base structure 200 of the biocompatible structure 90 can have different degradation rates. In one embodiment, the degradation rate of the first base structure 100 is slower than the degradation rate of the second base structure 200.

When placed in an implant site, new tissue of a patient can grow across the pores on the surface of the biocompatible structure, and inside the hollow interior of the biocompatible structure.

In certain embodiments, each of the first base structure 100 and the second base structure 200 of a biocompatible structure 90 can be seeded with the corresponding types of cells (or stem cells) for each tissue. For example, bone forming cells can be seeded to the first base structure 100, and muscle cells can be seeded to the second base structure 200.

In certain embodiments, each of the base structures in the biocompatible structure 90 can be decorated with antibiotics and or with corresponding growth factors.

In certain embodiments, each of the base structures can be doped with various nanomaterials both in the bulk as well as on the surface.

In certain embodiments, when placed in the implant site 50, due to its morphological characteristics, the biocompatible structure 90 absorbs liquid from the implant site 50 quickly, and expands about 2-5% in volume, such that the biocompatible structure 90 locks itself into the implant site 50 and stays well attached. In certain embodiments, according to the components of the biocompatible structure 90 having the first base structure 100 and the second base structure 200, the condition of the patient, and the implant site 50, the biocompatible structure 90 expands about 1-50% in volume after being placed in the implant site 50. In one embodiment, the biocompatible structure 90 expands up to about 10-15% in volume after being placed in the implant site 50. In one embodiment, the biocompatible structure 90 expands about 2-5% in volume after being placed in the implant site 50. In one embodiment, the biocompatible structure 90 expands about 4% in volume after being placed in the implant site 50. In certain embodiments, the first base structure 100 portion and the second base structure 200 portion of the biocompatible structure 90 can have different expansion rate. For example, each of the first base structure 100 and the second base structure 200 of the biocompatible structure 90 has an expansion rate consistent with the requirement of their corresponding tissue portion of the implant site 50. In certain embodiments, according to the components of the biocompatible structure 90 having the first base structure 100 and the second base structure 200, the condition of the patient, and the implant site 50, the first base structure 100 expands about 0-8% in volume after being placed in the bone area 500 of the implant site 50, and the second base structure 200 expands about 1-10% in volume after being placed in the muscle area 600 of the implant site 50. In certain embodiments, the expansion of the first base structure 100 portion is lower than the expansion of the second base structure 200 portion. In one embodiment, the first base structure 100 expands about 1-5% in volume after being placed in the bone area 500, and the second base structure 200 expands about 2-6% in volume after being placed in the muscle area 600. In one embodiment, the first base structure 100 expands about 3% in volume after being placed in the bone area 500, and the second base structure 200 expands about 4% in volume after being placed in the muscle area 600.

In certain embodiments, according to the components of the biocompatible structure 90 having the first base structure 100 and the second base structure 200, the condition of the patient, and the condition of the implant site 50, the expansion may occur at the first 30 days of the implantation process. In one embodiment, the expansion occurs in the first 5 days of the implantation. In one embodiment, the expansion occurs in the first 24 hours of the implantation. In one embodiment, the expansion occurs in the first 12 hours of the implantation. In one embodiment, the expansion occurs in the first 6 hours of the implantation.

In one embodiment, the implant stabilized in the first 10 days. That is, the implant does not have substantially expansion after the first 10 days. In one embodiment, the implant stabilized in the first 5 days. In one embodiment, the implant stabilized in the first 24 hours. In one embodiment, the implant stabilized in the first 12 hours. In one embodiment, the implant stabilized in the first 6 hours.

In certain embodiments, the occurrence time of the expansion and the lasting period of the expansion for the first base structure 100 are different from those of the second base structure 200.

Figure 3A:
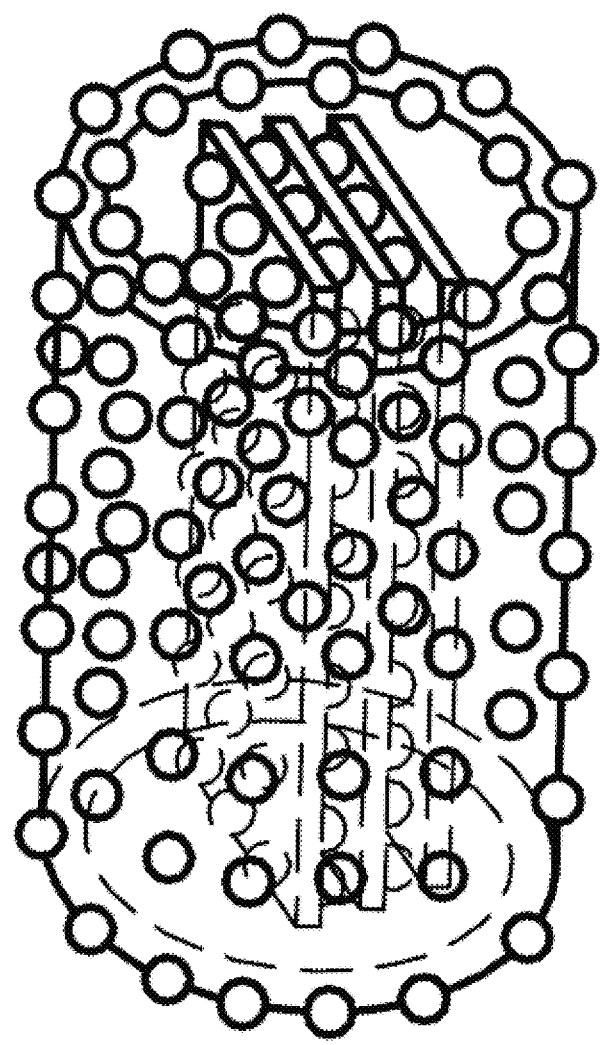
FIG. 3A illustrates a biocompatible structure having one base structure according to certain embodiments of the present disclosure.

FIG. 3A illustrates a biocompatible structure 30 having one base structure according to certain embodiments of the present disclosure.

Figure 3B:
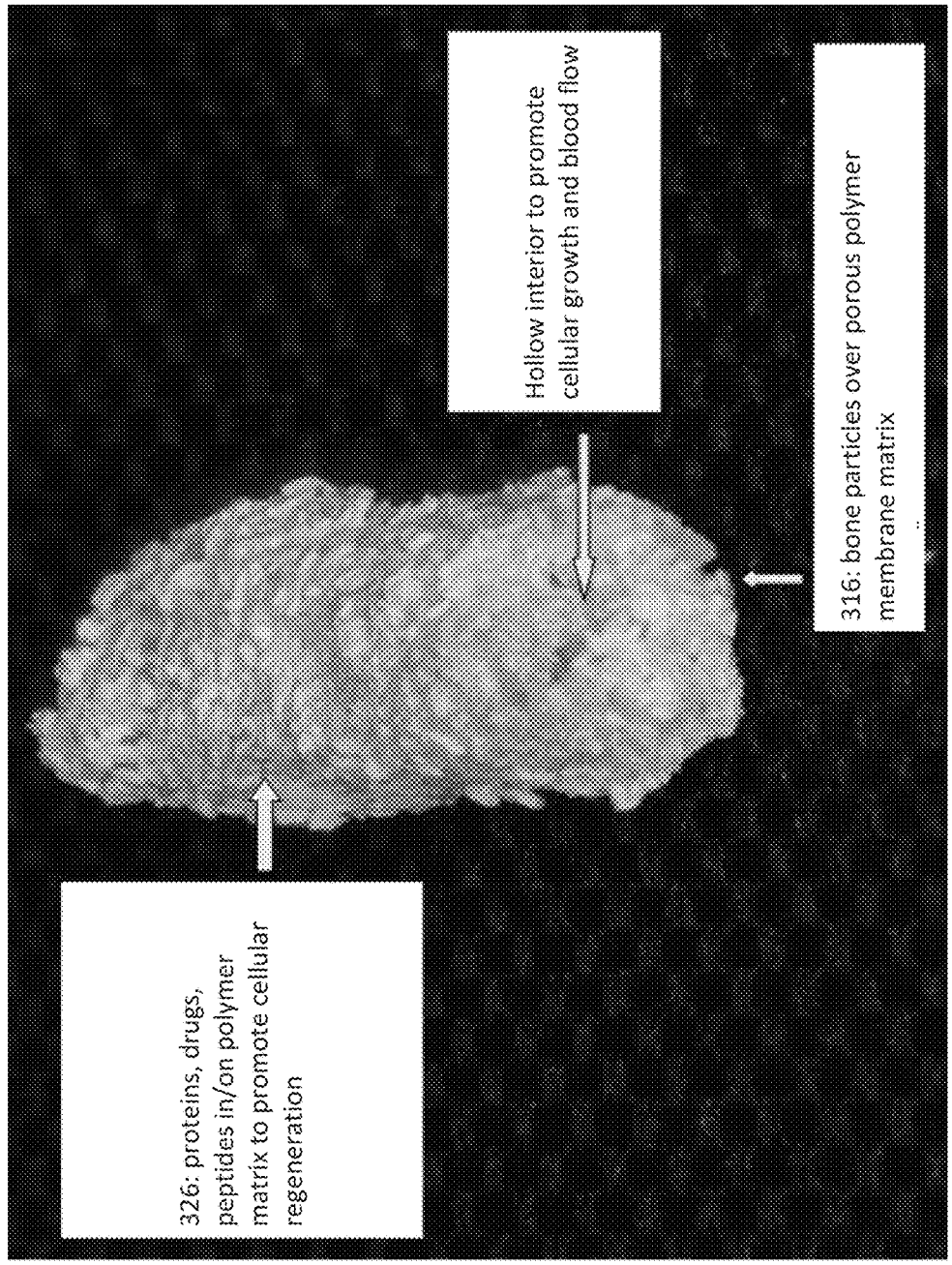
FIG. 3B schematically shows a Scanning Electron Microscopy image of a biocompatible structure at a low resolution according to certain embodiments of the present disclosure.

FIG. 3B schematically shows a Scanning Electron Microscopy image of the biocompatible structure 30 having one base structure at a low resolution according to certain embodiments of the present disclosure. The biocompatible structure 30 has bone particles 316 over porous polymer membrane matrix and a hollow interior to promote cellular growth and blood flow. In FIG. 3B, bioactive materials 326 are shown on the surface of the biocompatible structure 30. In certain embodiments, the bioactive materials 326 can be sprayed on the surface of the biocompatible structure 30, and/or incorporated in the polymer layer to promote bone growth.

Figures 3C, 3D, 3E:
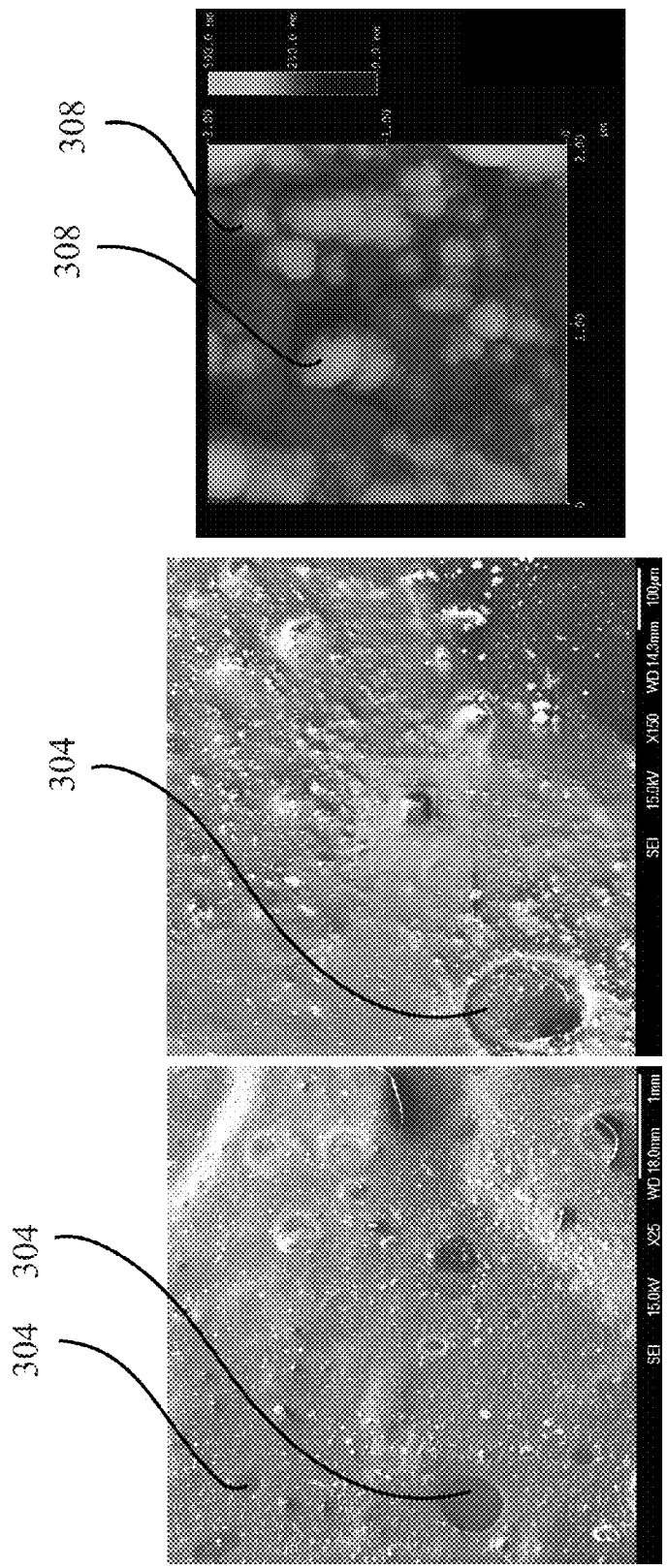
FIGS. 3C-3E schematically show Scanning Electron Microscopy images of a biocompatible structure at a high resolution according to certain embodiments of the present disclosure.

FIGS. 3C-3E schematically shows Scanning Electron Microscopy images of the biocompatible structure 30 having one base structure at high resolutions according to certain embodiments of the present disclosure. As shown in FIGS. 3C-3E, the surface of the biocompatible structure 30 made from polyurethane polymer and hydroxyapatite nanoparticles can be very rough and can have one or more polymeric pores 304. The polymeric pores 304 typically are large in size. The size of the polymeric pores 304 can be from about 0.001 µm up to about 10 mm. The nanostructural hydroxyapatatite 308 at the surface of the biocompatible structure 30 can have a size of about 1 nm to about 500 nm, and the majority of the nanostructural hydroxyapatite 308 can have a size of about 2 nm to about 300 nm. Inside the biocompatible structure 30 is semi-empty due to the spacing between the layers offered by the bone particles. The pore size should vary both in the range of nanometer (nm) and the range of micrometer (µm).

In certain embodiments, the biocompatible structure 90 useful for bone and tissue regeneration includes one or more base structures. The biocompatible structure 90 having two base structures 100 and 200 can be produced by the following procedures.

Figure 4A:
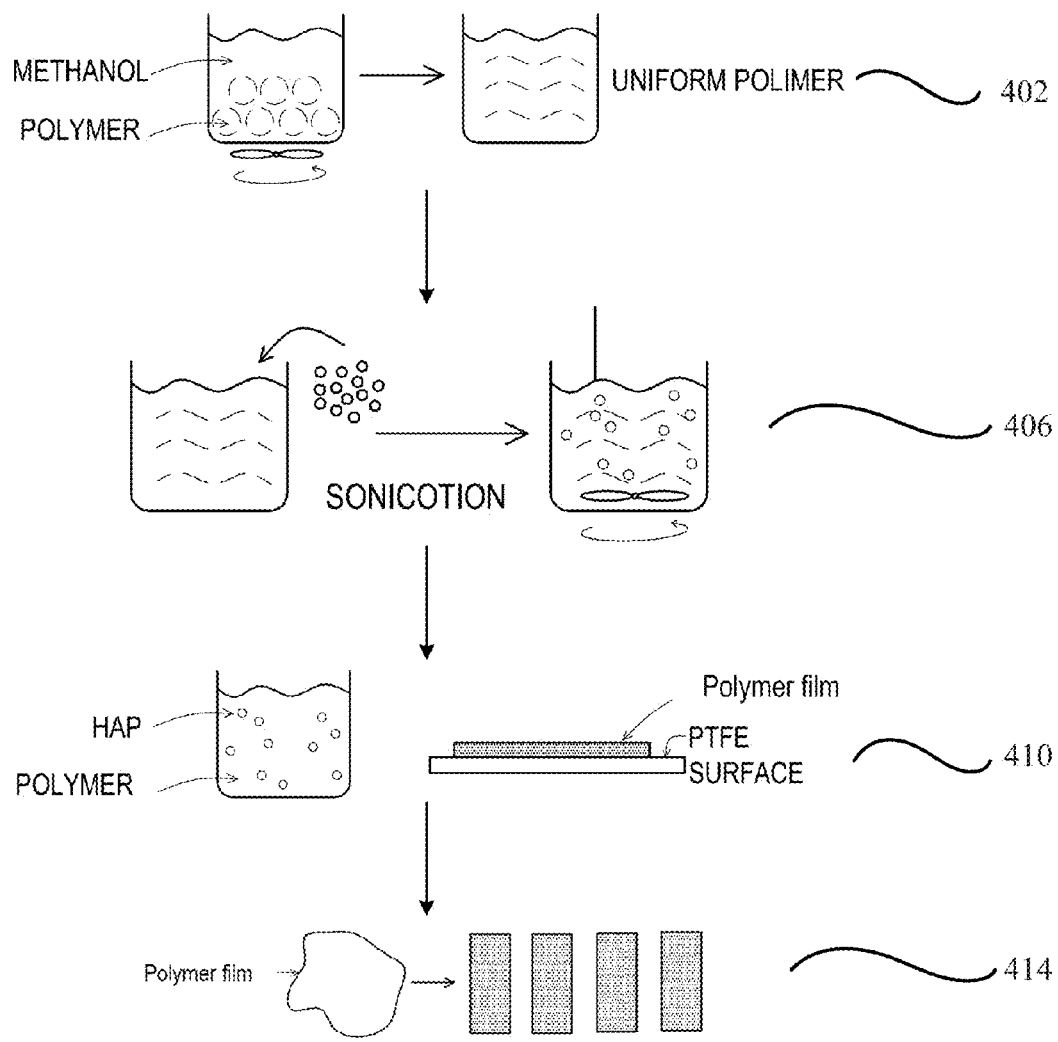
FIGS. 4A and 4B schematically shows procedures for producing a biocompatible structure having two base structures according to certain embodiments of the present disclosure.

As shown in FIG. 4A, in operation 402, a first polymer 114 is dissolved in a first solvent to form a first solution.

In certain embodiments, the first polymer 114 can be a synthetic biodegradable polymer, a biodegradable polymer derived from natural source, or their mixture. In certain embodiment, suitable synthetic biodegradable polymer may include polyurethane, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, polyphosphazene, or their mixture. In certain embodiments, the biodegradable polymer derived from natural source may include modified polysaccharides (cellulose, chitin, dextran), modified proteins (fibrin, casein), or their mixture.

In certain embodiment, the first polymer 114 is ester-type hydrophilic polyurethane with a linear expansion of 50-65%. The water uptake of the first polymer 114 varies with its composition, anywhere from 30-90%. The first polymer 114 is thermoplastic. Alternatively, a thermosetting first polymer 114 may work equally well. In certain embodiment, the first polymer 114 may be mixed with other polymers to control its degradation rate. In certain embodiment, the polymer is a powder with particles having a diameter of about 0.02-50 mm.

The first solvent can be methanol or ethanol or any solvent of the polymer used. In certain embodiment, other organic or inorganic solvent (polar aprotic and protic) may also be used. In certain embodiments, the solvent is at least one of acetone, methyl ethyl ketone, nitromethane, n-propanol, n-butanol, isopropanol, propylene carbonate, dymethil sulfoxide, acetonitrile, dimethylformamide, ethyl acetate, and tetrahydrofuran, dichloromethane.

The first polymer 114 is evenly distributed in the first solution. In certain embodiment, low power heating can be used to help the dissolution of the polymer in the solvent. In certain embodiments, stirring is used to accelerate the uniform distribution of the polymer in the first solution. In certain embodiment, after complete dissolvation of the solid polymer in the solvent, the first solution has a low viscosity.

In operation 406, the first tissue forming nanoparticles 112 are added to the first solution to form a second solution.

In certain embodiments, the first tissue forming material 112 may include nanoparticles of hydroxyapatite (HAP), tricalcium phosphates, mixed calcium phosphates and calcium carbonate, bone particles of zenograft, allografts, autografts, alloplastic grafts, or a mixture thereof.

In certain embodiment, the HAP nanoparticles 112 have a dimensional range between 1-100 nm. The HAP nanoparticiels 112 can be composed of pure HAP, having significant crystallinity, and having very good dispensability due to the presence of oxygen groups on the surface.

The first polymer 114 and the first tissue forming material 112 are evenly distributed in the second solution. In certain embodiments, sonication is used to accelerate the homogenization of the first polymer 114 and the first tissue forming material 112 in the second solution.

The weight percentage of the first polymer 114 to the first tissue forming material 112 in the second solution is about 20:1 to 2:1. The ratio is related with the characteristics of the produced first base structure 100. The characteristics of the first base structure 100 include resistance to load and stress, porosity, degradation rate, etc. In certain embodiments, the ratio of the polymer first 114 to the first tissue forming material 112 can be adjusted to meet requirement of the condition of a patient, including the bone or muscle implant position, size, and metabolic rate of the patient.

In certain embodiment, the first polymer 114 is polyurethane and the first tissue forming material 112 is HAP nanopowder containing HAP nanoparticles. The weight ratio of the added dry HAP nanopowder to the dry mass of the added polymer varies according to the purpose of use.

In certain embodiment, as described below in connection with FIGS. 8-9, if the first weight ratio of the dry HAP nanopowders to the dry mass of polyurethane is below 25% (i.e., the weight percentage of dry HAP nanopowder in the total weight of dry HAP nanopowder and dry mass of polymer is about 20%), the produced first polymer film 102 as described below is strong and hard. If the first weight percentage of the dry HAP nanopowders to the polyurethane is above 40%, the produced the polymer film as described below is weak and breaks easily. In certain embodiment, the HAP nanoparticles 112 do not allow a good crosslinking of the polymer strands. Therefore the first polymer film produced with a high ratio of HAP nanoparticles 112 is very powdery and breaks very easily.

In operation 410, the second solution is applied to a first surface to form a first polymer film on the surface. A first weight percentage of the first tissue forming nanoparticles 112 to the polymer is about 0.5-95%.

In certain embodiment, the first polymer film is formed by applying the second solution to the first surface, and allowing it to dry. In certain embodiment, the second solution can be dried at a room temperature (e.g., 25° C.). In certain embodiment, the second solution is mildly heated to form the polymer film on the surface, for example, at a temperature higher than room temperature (e.g., 25° C.) and lower than 80° C. In certain embodiment, the drying process is under a vacuum condition. In certain embodiment, the surface is a Teflon surface. In certain embodiment, the first surface is a polytetrafluoroethylene (PTFE) surface. In certain embodiment, the second solution can be dried on a PTFE surface under vacuum and under mild heat for less than 24 hours to form the polymer film. The thickness of the polymer film can be about 2-10 mm.

In operation 414, the first polymer film is cut into a plurality of first strips, i.e., the first polymer layers 102.

The first layers 102 can be cut into any suitable shape and size to produce a biocompatible structure with a predetermined shape and size. In certain embodiment, each of the first layers 102 is identical to other strips. In certain embodiment, each of the strips has a length of about 0.002-50 cm, a width of about 0.002-50 cm, and a thickness of about 0.001-50 mm.

At the same time or sequentially, multiple second strips 202 can be produced using the material and process as disclosed in the above operations 402 to 414. Specifically, as shown in the operation 402, a second polymer 214 is dissolved in a second solvent to form a third solution. As shown in the operation 406, the second tissue forming nanoparticles 212 are added to the third solution to form a fourth solution. The second weight percentage of the second polymer 214 to the second tissue forming material 212 in the fourth solution is about 20:1 to 2:1. In certain embodiments, the ratio of the second polymer 214 to the second tissue forming material 212 can be adjusted to meet requirement of the condition of a patient, including the bone or muscle implant position, size, and metabolic rate of the patient. As shown in the operation 410, the fourth solution is applied to a second surface to form a second polymer film on the second surface. A second weight percentage of the second tissue forming material to the polymer is about 0.5-95%. As shown in the operation 414, the second polymer film is cut into a plurality of second strips, i.e., the second polymer layers 202.

In certain embodiments, the second nanoparticles 212 can be the same as or different from the first nanoparticles 112. In certain embodiments, the second polymer 214 can be the same as or different from the first polymer 114. In certain embodiments, the second solvent can be the same as or different from the first solvent. In certain embodiments, the second surface can be the same as or different from the first surface. In certain embodiment, the second surface is the first surface. In certain embodiment, the second weight percentage is different from the first weight percentage, such that the first layers 102 is harder than the second strips 202, that is, the density of the first layers 102 is greater than the density of the second strips 202. In certain embodiment, both the first tissue forming nanoparticles 112 and the second tissue forming nanoparticles 212 are HAP nanoparticles. In other embodiments, at least one of the first tissue forming nanoparticles 112, the first polymer 114, the first solvent, and the first weight percentage is different from the corresponding second tissue forming nanoparticles 212, second polymer 214, second solvent, and second weight percentage. In certain embodiments, the second tissue forming nanoparticles 212 are polymeric nanoparticles or nanofibers.

Figure 4B:
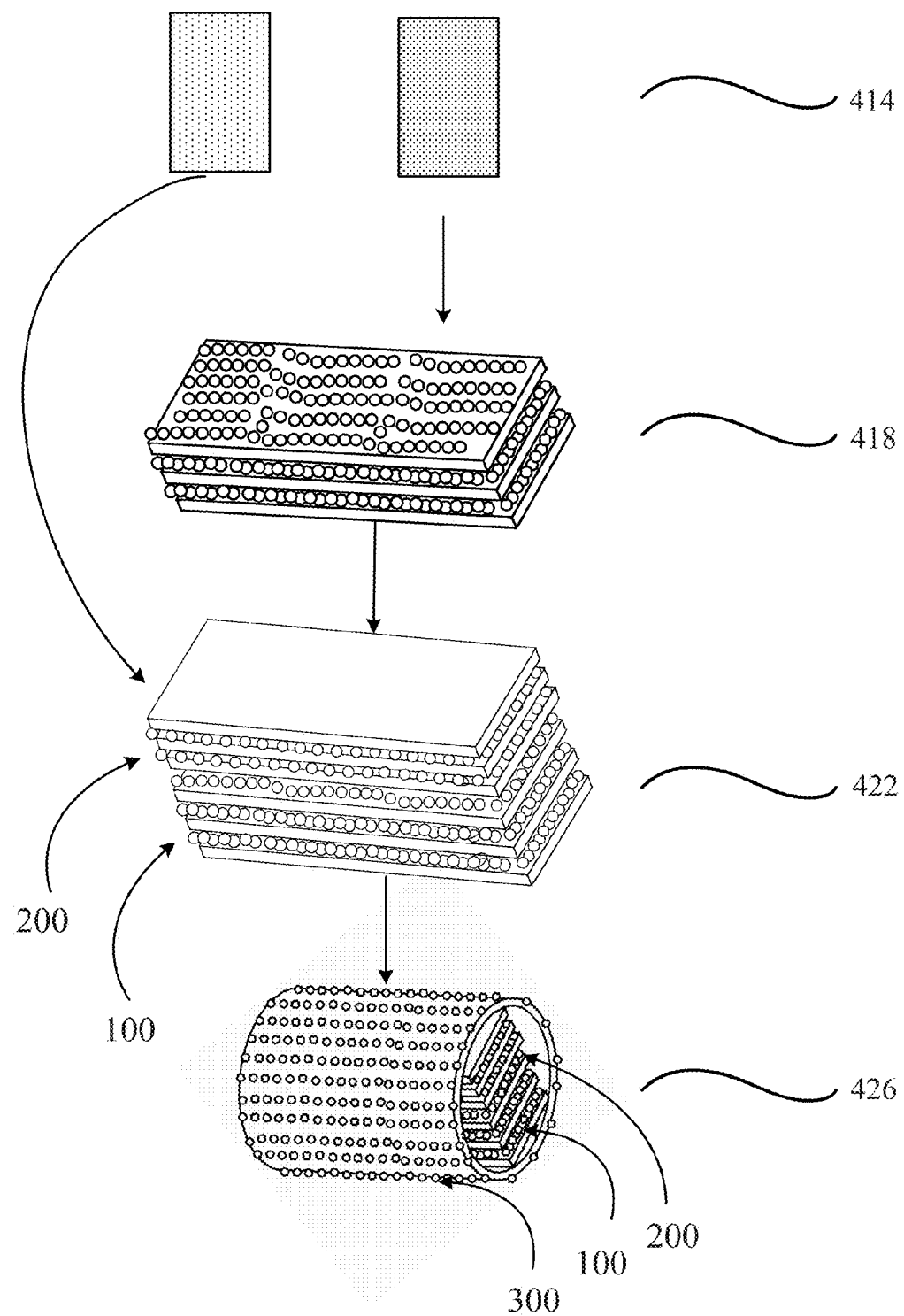

As shown in FIG. 4B, the biocompatible structure 90 is formed by stacking the first layers 102, the first bone particle layers 106, the second strips 202, and the second bone particle layers 206. Then the structure is coated by a coating 300 formed from a fifth solution, and the third bone particles 316 are then added onto the surface of the coating 300. The fifth solution can be the same or different from the second solution and/or the fourth solution.

Only three first polymer layers 102-1, 102-2, and 102-3 and three second polymer layers 202-1, 202-2, 202-3 are shown in FIG. 4B. However, as shown in FIG. 2B, the number of the first polymer layers 102 can be m, and the number of the second polymer layers can be n, where m and n are positive integers.

In certain embodiments, as shown in operation 418, the first polymer layer 102-1 is disposed on a surface, the first spacer layer 106-1 is stacked on the first polymer layer 102-1, the first polymer layer 102-2 is stacked on the first spacer layer 106-2, the first spacer layer 106-2 is stacked on the first polymer layer 102-2, the first polymer layer 102-3 is stacked on the first spacer layer 106-2, and the first spacer layer 106-3 is stacked on the first polymer layer 102-3. By alternatively disposing first polymer layers 102 and first spacer layers 106, the first base structure 100 with a predetermined shape and size is constructed. In certain embodiments, at least one first polymer layer 102 is located as one of the outside layers of the first base structure 100. In certain embodiment, at least one first spacer layer 106 is located as one of the outside layers of the first base structure 100.

In certain embodiments, as shown in operation 422, the second polymer layer 202-1 is disposed on the first spacer layer 106-3, the second spacer layer 206-1 is stacked on the second polymer layer 202-1, the second polymer layer 202-2 is stacked on the second spacer layer 206-1, the second spacer layer 206-2 is stacked on the second polymer layer 202-2, and the second polymer layer 202-3 is stacked on the second spacer layer 206-2. By alternatively disposing second polymer layers 202 and second spacer layers 206, the second base structure 200 with a predetermined shape and size is constructed. In certain embodiments, a polymer layer 202 is located as the most outside layer of the second base structure 200. In certain embodiment, a second spacer layer 206 is located as one of the most outside layer of the second base structure 200. In certain embodiments, a second polymer layer 202 is located as the most inner side layer adjacent to the first base structure 100. In certain embodiment, a second spacer layer 206 is located as the most inner side layer adjacent to the first base structure. Thus the interface between the first base structure 100 and the second base structure 200 can be a first polymer layer 102-second polymer layer 202 interface, a first polymer layer 102-second spacer particle layer 206 interface, a first spacer layer 106-second polymer layer 202 interface, or a first spacer layer 106-second spacer layer 206 interface.

In certain embodiments, as shown in FIG. 4B, the first base structure 100 and the second base structure 200 are formed in one step of the operations 418 and 422 by stacking the first polymer layers 102 and the first spacer layers 106 alternately, and stacking the second polymer layers 202 and the second spacer layers 106 alternately on the alternately disposed first polymer layers 102 and the first spacer layers 106.

The operation 422 can further include liquefying the stacked first base structure 100 and the second base structure 200. In order for the entire structure to stay together, methanol or other solvent of the polymer is added by, for example pipetting, to superficially liquefy the polymer layers 102 and 202, such that the spacer particles 116 and 226 can be "trapped" in the polymer layers 102 and 202 when the structure dries. The spacer particles 116 and 216 can be partially embedded in the polymer layers 102 and 202. After the polymer layers 102 and 202 re-solidifies, the bone particle layers 106 and 206 are connected with the polymer layers 102 and 202.

In this embodiment, the first base structure 100 and the second base structure 200 are liquefied in one operation. In certain embodiments, the liquefying solution can be methanol or any other solvent, the first solution, the second solution, the third solution, the fourth solution, or any other solution that can liquefy the base structures. In certain embodiments, the first base structure 100 and the second base structure 200 can be liquefied using the same solution or different solutions. In certain embodiments, the first base structure 100 and the second base structure 200 are produced separately, liquefied separately, dried separately, and then stacked together.

In certain embodiments, when a biocompatible structure having more than two base structures is needed, then the above process includes stacking more than two, for example, 3, 4, 5, 6 or more base structures together.

In operation 426, a fifth solution is applied to the stacked structure of the first base structure 100 and the second structure 200 to form a coated structure. In certain embodiments, the fifth solution is the second solution or the fourth solution. In certain embodiment, the weight percentage of the tissue forming nanoparticles in the fifth solution is between the first weight percentage of the tissue forming nanoparticles in the second solution and the second weight percentage of the tissue forming nanoparticles in the fourth solution. In certain embodiments, the stacked structure built as described above is then coated by covering with a polymer film that is in a liquid form. In certain embodiment, the fifth solution is a sticky solution before applying to the stacked structure. In certain embodiment, part of the fifth solution poured on the surface of the stacked structure penetrates to the inside of the stacked structure. The poured fifth solution forms a coat 300 on the surface of the stacked structure and helps to hold the components of the stacked structure together.

In certain embodiment, the operation 426 further includes adding the third spacer particles 316 to the coated structure to form the biocompatible structure 90. In certain embodiment, the third spacer particles 316 can be nano-sized bone particles, micro-sized bone particles, or a mixture thereof. The structure is then allowed to dry overnight under vacuum and mild heat to form the biocompatible structure 90 according to the present disclosure.

The biocompatible structure 90 can be any shape and size such that the biocompatible structure 90 matches the size of the bone defect that needs to be regenerated. In certain embodiment, the biocompatible structure 90 has a cylindrical shape or a spherical shape. In certain embodiment, the length of the biocompatible structure 90 is about 2.5 cm (1 inch) and the diameter is about 0.1-1 cm, which matches the diameter of the bone that needs to be replaced.

In certain embodiment, the method further includes subjecting the biocompatible structure 90 having one or more base structures to plasma treatment. For example, once completely dried, the biocompatible structure 90 is placed into glass vials for storage. The biocompatible structure 90 is plasma treated by a radio frequency (RF) plasma discharge device, under an environment of oxygen, nitrogen or a mixture of oxygen and nitrogen. In certain embodiment, the RF plasma treatment time is about 10-30 minutes. In certain embodiment, the RF plasma treatment time is about 5-15 minutes. In certain embodiment, the RF plasma treatment time is about 1-3 minutes. In certain embodiment, the plasma treated biocompatible structure 90 is sterilized and sent for animal studies. The purpose of the plasma treatment is to break the surface bonds of the polymer. After plasma treatment, oxygen atoms "attach" to the surface, changing the surface energy of the surface such that the surface becomes more hydrophilic and has oxygen and nitrogen rich functional groups.

In certain embodiment, the method of manufacturing the biocompatible structure 90 further includes adding a third tissue forming material 326 to the biocompatible structure 90. In certain embodiment, the third tissue forming material 326 includes a bioactive material, cells, or a mixture thereof. The bioactive material includes proteins, enzymes, growth factors, amino acids, bone morphogenic proteins, platelet derived growth factors, vascular endothelial growth factors, or a mixture thereof. The cells includes epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof. In certain embodiments, the third tissue forming material 326 located in the part of the surface of the biocompatible structure 90 corresponding to the first base structure 100 is different from the third tissue forming material 326 located in the part of the surface of the biocompatible structure 90 corresponding to the second base structure 200.

Figure 5:
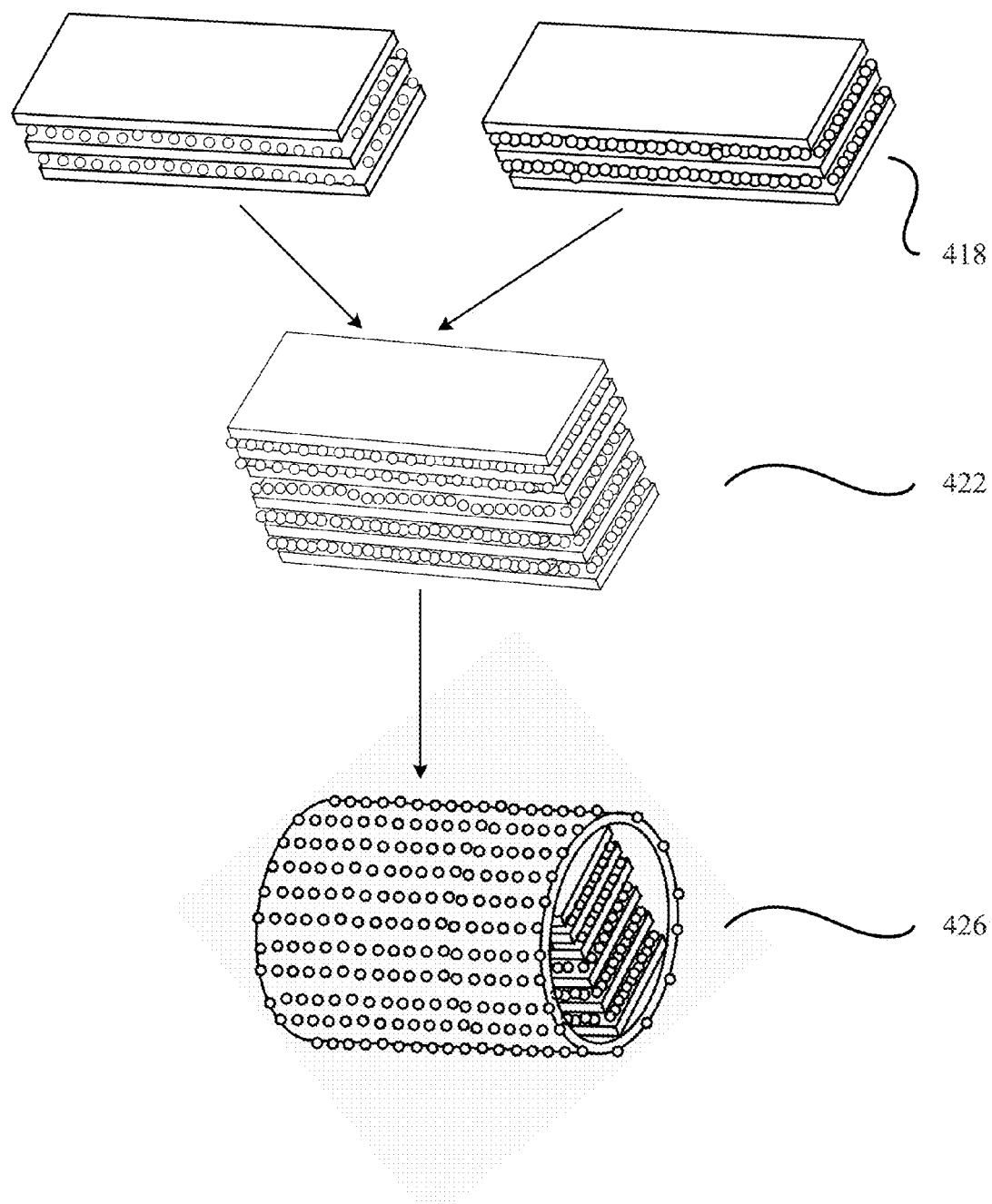
FIG. 5 schematically shows procedures for producing a biocompatible structure having two base structure according to certain embodiments of the present disclosure.

In other embodiments, as shown in FIG. 5, the first base structure 100 and the second base structure 200 can be formed independently on the same or separated surfaces, and then stacked the first base structure 100 and the second base structure afterwards, coating the stacked structure, and optionally plasma treating to form the biocompatible structure.

Figure 6:
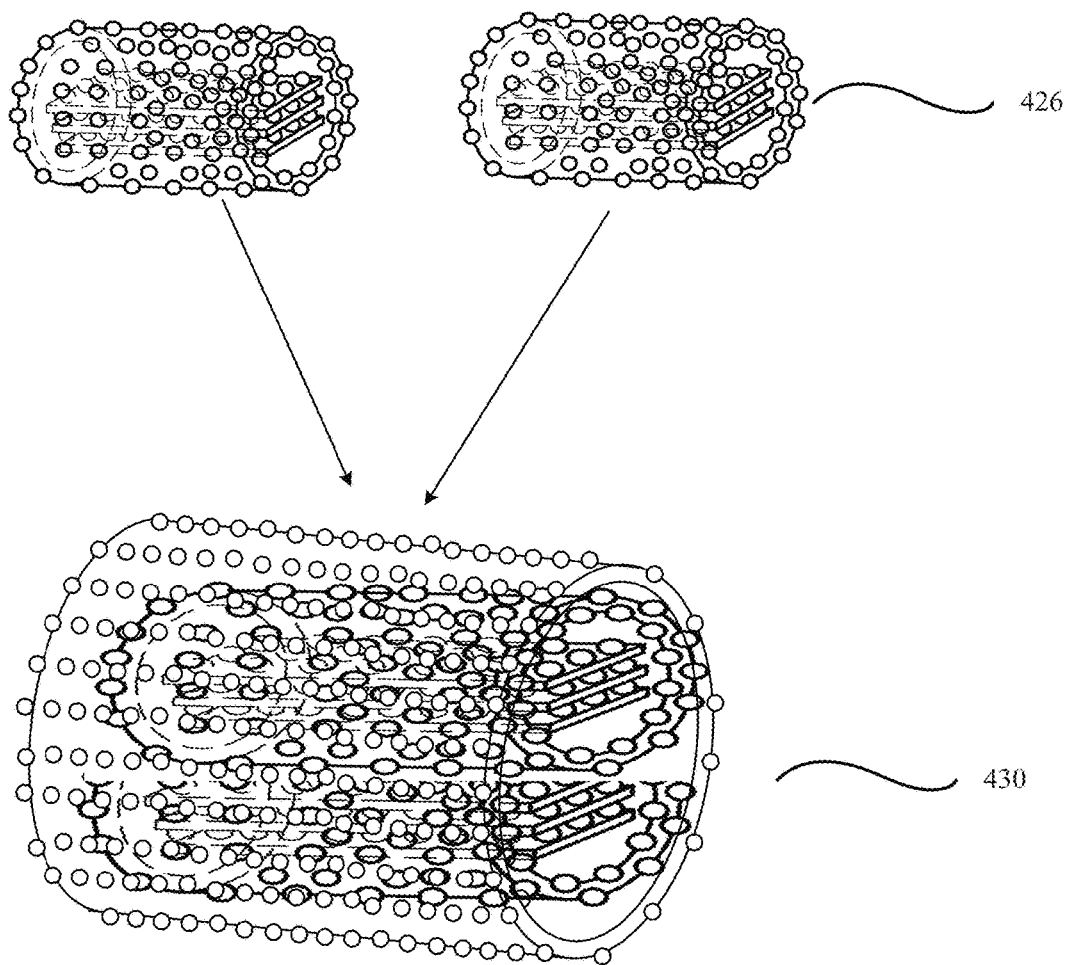
FIG. 6 schematically shows procedures for producing a biocompatible structure having two base structures according to certain embodiments of the present disclosure.

Alternatively, as shown in FIG. 6, the first base structure 100 can be coated and optionally treated to form a first biocompatible sub-structure. The second base structure 100 can be coated and optionally plasma treated for form a second biocompatible structure. The first biocompatible sub-structure and the second biocompatible sub-structure are then stacked together, coated, and optionally plasma treated to form the biocompatible structure. Alternatively, the combination of the coated, dried and optionally plasma treated first biocompatible sub-structure and second biocompatible sub-structure can be performed, instead of another coating process, by binding through an organic binder, or by any other means such that the first biocompatible sub-structure and the second biocompatible sub-structure are stably combined as one unity.

In certain embodiment, instead of manufacturing the biocompatible structure 90 and then using it as implant material, the biocompatible structures 90 can also be formed in situ. For example, a first polymer layer is air sprayed at an implant site or a bone defect area, a first layer of bone particles is then added to the polymer layer and deposits on the polymer layer. After that, a second polymer layer is air sprayed on the first bone particle layer, followed by adding a second layer of bone particles. The process is repeated until the biocompatible structure, including alternating polymer layers and bone particle layers, matches the implant site or mimics the bone defect that needs to be replaced. The biocompatible structure 90 formed in situ can also include one or more base structures. For example, a series of alternatively stacked first polymer layer and first bone particle layer is formed first, corresponding to a bone area 500; then a series of alternatively stacked first polymer layer and first bone particle layer is formed first, corresponding to a muscle area 600.

In certain embodiment, a Doctor of Medicine (MD) can take a 3D computer axial tomography scan (CAT) of a patient and sent the result for example by emailing the CAT scan file to a manufacturer. The manufacturer then can build the implant according to the present disclosure to perfectly match the actual bone defect.

One example is provided according to the process shown in FIG. 4A and FIG. 4B.

In operation 402, 500 ml methanol is added to a 1 L beaker. The beaker is placed on a magnetic stirrer and a magnetic stir bar is used for mixing. 80 grams polyurethane 114 is then added to the methanol in the beaker. The solution is mixed by the stirring bar to completely dissolve the polyurethane in the methanol solvent and uniformly distributed the polyurethane 114 in the solution. The mixing and dissolving of polyurethane is at room temperature. In certain embodiment, the solution can be heated to accelerate the process.

In operation 406, 20 gram HAP nanoparticles 112 (e.g., Berkeley Advanced Biomaterials, Inc.) is then added to the solution. Sonication is applied to guarantee the evenly distribution of the HAP nanoparticles 112 in the solution.

In operation 410, 10 ml of the solution is pipetted from the beaker and applied to a PTFE surface. A thin layer of solution is formed on the PTEF surface. The thin layer of solution is allowed to dry at room temperature for variable times to form a polymer film. Alternatively, the layer of solution on the PTFE surface can be placed in an oven to heat or low pressure for a period of time to accelerate the formation of the polymer film. In certain embodiment, the temperature can be about 30-70° C., and the period of time for the heating is about 2-1500 minutes. In certain embodiment, the second solution is allowed to dry on a PTFE surface under vacuum under mild heat for less than 24 hours to form the polymer film. The thickness of the polymer film can be about 0.01-50 mm.

In operation 414, the polymer film is then cut into identical strips with a length of about 0.05-20 cm, a width of about 0.02-5 cm, and a thickness of about 0.01-50 mm. In certain embodiment, the polymer film can be cut into strips with varies shape and size. Those strips are first polymer layers 102.

The operations 402, 406, 410 and 414 can be used to prepare the first plurality of layers 102. In the same matter, the operations 402, 406, 410 and 414 can be used to prepare the second polymer layers 202. The weight percentage of HAP nanoparticles in the total weight of the first polymer layers 102 is different from that in the second polymer layers 202. In one embodiment, the first weight percentage of HAP nanoparticles in the total weight of the first polymer layers 102 is about 15-30%. In one embodiment, the first weight percentage of HAP nanoparticles in the total weight of the first polymer layers 102 is about 17-23%. In one embodiment, the first weight percentage of HAP nanoparticles in the total weight of the first polymer layers 102 is about 20%. In one embodiment, the second weight percentage of HAP nanoparticles in the total weight of the second polymer layers 202 is about 10-25%. In one embodiment, the second weight percentage of HAP nanoparticles in the total weight of the second polymer layers 202 is about 15-20%. In one embodiment, the second weight percentage of HAP nanoparticles in the total weight of the second polymer layers 202 is about 18%. In certain embodiments, the first weight percentage is greater than the second weight percentage. In certain embodiments, the first weight percentage is 0.1-50% greater than the second weight percentage. In certain embodiments, the first weight percentage is 0.5-10% greater than the second weight percentage. In certain embodiments, the first weight percentage is 1-5% greater than the second weight percentage. In certain embodiments, the first weight percentage is 2% greater than the second weight percentage.

In certain embodiments, as shown in operation 418, the first polymer layer 102-1, the first spacer layer 106-1, the first polymer layer 102-2, the first spacer layer 106-2, the first polymer layer 102-3, the first spacer layer 106-3 . . . the first spacer layer 106-m, the second polymer layer 202-1, the second spacer layer 206-1, the second polymer layer 202-2, the second spacer layer 206-2, the second polymer layer 202-3 . . . the second polymer layer 202-n are stacked to form a three dimensional structure.

In this example, the spacer particles 116 of the first spacer layers 106 and the spacer particles 216 of the second spacer layers 206 are bone particles. In certain embodiments, the bone particle density and the thickness of the first bone particles 116 are different from those of the second bone particles 216. In certain embodiments, the density of the first bone particles 116 is greater than the density of the bone particles 216.

After stacking of the three dimensional structure, in order for the entire structure to stay together, methanol or other solvent of the polymer is added by, for example pipetting, to superficially liquefy the polymer layers 102 and 202, such that the bone particles 116 and 206 can be "trapped" in the polymer layers 102 and 202 when the structure dries. The bone particles 116 and 216 can be partially embedded in the polymer layers 102 and 202. After the polymer layers 102 and 202 re-solidifies, the bone particle layers 106 and 206 are connected with the polymer layers 102 and 202. Alternatively, the liquefying step can be performed two or more times during the stacking of the three dimensional structure.

In operation 426, a certain volume, for example 1 ml, of the methanol/polyurethane/HAP nanoparticle solution is added to the surface of the three-dimensional structure and allowed to dry. In one embodiment, the methanol/polyurethane/HAP nanoparticle solution is the second solution or the fourth solution. Accordingly, a coating 300 is formed on the surface of the three-dimensional structure to form a coated structure. In certain embodiment, the coating 300 not only covers the outside of the three-dimensional structure, but also can penetrate to the inside of the three-dimensional structure.

Further, a third spacer particles 316, which could be the same as the first bone particles 116 and second bone particles 216, or other suitable particles, may be added to the surface of the coating 300.

In certain embodiment, the coated structure is then dried under vacuum overnight. In certain embodiment, the structure is further subjected to plasma treatment to form the biocompatible structure 90. The plasma treatment may be a nitrogen or oxygen plasma treatment.

In certain embodiment, the first base structure 100 and the second base structure 200 of the biocompatible structure 90 are configured for the regeneration of two different portions of a bone loss/implant site, where the first base structure 100 corresponds to a hard portion of the bone loss and the second base structure 200 corresponds to a softer portion of the bone loss.

One example is provided according to the process shown in FIG. 4A and FIG. 4B.

In operation 402, 500 ml methanol is added to a 1 L beaker. The beaker is placed on a magnetic stirrer and a magnetic stir bar is used for mixing. 80 grams polyurethane 114 is then added to the methanol in the beaker. The solution is mixed by the stirring bar to completely dissolve the polyurethane in the methanol solvent and uniformly distributed the polyurethane 114 in the solution. The mixing and dissolving of polyurethane is at room temperature. In certain embodiment, the solution can be heated to accelerate the process.

In operation 406, 20 gram HAP nanoparticles 112 (e.g., Berkeley Advanced Biomaterials, Inc.) is then added to the solution. Sonication is applied to guarantee the evenly distribution of the HAP nanoparticles 112 in the solution.

In operation 410, 10 ml of the solution is pipetted from the beaker and applied to a PTFE surface. A thin layer of solution is formed on the PTEF surface. The thin layer of solution is allowed to dry at room temperature for variable times to form a polymer film. Alternatively, the layer of solution on the PTFE surface can be placed in an oven to heat or low pressure for a period of time to accelerate the formation of the polymer film. In certain embodiment, the temperature can be about 30-70° C., and the period of time for the heating is about 2-1500 minutes. In certain embodiment, the second solution is allowed to dry on a PTFE surface under vacuum under mild heat for less than 24 hours to form the polymer film. The thickness of the polymer film can be about 0.01-50 mm.

In operation 414, the polymer film is then cut into identical strips with a length of about 0.05-20 cm, a width of about 0.02-5 cm, and a thickness of about 0.01-50 mm. In certain embodiment, the polymer film can be cut into strips with varies shape and size. Those strips are first polymer layers 102.

The operations 402, 406, 410 and 414 can be used to prepare the first plurality of layers 102. In the same matter, the operations 402, 406, 410 and 414 can be used to prepare the second polymer layers 202, except that the second tissue forming material 212 is nanofiber or polymeric nanoparticles. The weight percentage of HAP nanoparticles in the total weight of the first polymer layers 102 is different from the nanofibers in the second polymer layers 202. In one embodiment, the first weight percentage of HAP nanoparticles in the total weight of the first polymer layers 102 is about 15-30%. In one embodiment, the first weight percentage of HAP nanoparticles in the total weight of the first polymer layers 102 is about 17-23%. In one embodiment, the first weight percentage of HAP nanoparticles in the total weight of the first polymer layers 102 is about 20%. In one embodiment, the second weight percentage of nanofibers in the total weight of the second polymer layers 202 is about 10-25%. In one embodiment, the second weight percentage of nanofibers in the total weight of the second polymer layers 202 is about 15-20%. In one embodiment, the second weight percentage of nanofibers in the total weight of the second polymer layers 202 is about 18%. In certain embodiments, the first weight percentage is greater than the second weight percentage. In certain embodiments, the first weight percentage is 0.1-50% greater than the second weight percentage. In certain embodiments, the first weight percentage is 0.5-10% greater than the second weight percentage. In certain embodiments, the first weight percentage is 1-5% greater than the second weight percentage. In certain embodiments, the first weight percentage is 2% greater than the second weight percentage.

In certain embodiments, as shown in operation 418, the first polymer layer 102-1, the first spacer layer 106-1, the first polymer layer 102-2, the first spacer layer 106-2, the first polymer layer 102-3, the first spacer layer 106-3 . . . the first spacer layer 106-$m$, the second polymer layer 202-1, the second spacer layer 206-1, the second polymer layer 202-2, the second spacer layer 206-2, the second polymer layer 202-3 . . . the second polymer layer 202-$n$ are stacked to form a three dimensional structure.

In this example, the spacer particles 116 of the first spacer layers 106 are bone particles and the spacer particles 216 of the second spacer layers 206 are nanofibers or polymeric nanoparticles. In certain embodiments, the bone particle density and the thickness of the first bone particles 116 are different from those of the nanofibers or polymeric nanoparticles 216. In certain embodiments, the density of the first bone particles 116 is greater than the density of the nanofibers or polymeric nanoparticles 216.

After stacking of the three dimensional structure, in order for the entire structure to stay together, methanol or other solvent of the polymer is added by, for example pipetting, to superficially liquefy the polymer layers 102 and 202, such that the bone particles 116 and the nanofibers or polymeric nanoparticles 216 can be "trapped" in the polymer layers 102 and 202 when the structure dries. The bone particles 116 and the nanofibers 216 can be partially embedded in the polymer layers 102 and 202. After the polymer layers 102 and 202 re-solidifies, the bone particle layers 106 and nanofiber layer or polymeric nanoparticle layer 206 are connected with the polymer layers 102 and 202. Alternatively, the liquefying step can be performed two or more times during the stacking of the three dimensional structure.

In operation 426, a certain volume, for example 1 ml, of the methanol/polyurethane/HAP nanoparticle solution or methanol/polyurethane/nanofiber solution is added to the surface of the three-dimensional structure and allowed to dry. In one embodiment, the methanol/polyurethane/HAP nanoparticle solution methanol/polyurethane/nanofiber solution is the second solution or the fourth solution. Accordingly, a coating 300 is formed on the surface of the three-dimensional structure to form a coated structure. In certain embodiment, the coating 300 not only covers the outside of the three-dimensional structure, but also can penetrate to the inside of the three-dimensional structure.

Further, a third spacer particles 316, which could be the same as the first bone particles 116 or the second nanofibers or polymeric nanoparticles 216, or other suitable particles, may be added to the surface of the coating 300.

In certain embodiment, the coated structure is then dried under vacuum overnight. In certain embodiment, the structure is further subjected to plasma treatment to form the biocompatible structure 90.

In certain embodiment, the first base structure 100 and the second base structure 200 of the biocompatible structure 90 are configured for the regeneration of an implant site having bone loss and muscle loss. The first base structure 100 corresponds to the bone loss portion of the implant site, facilitating regeneration of bone tissue. The second base structure 200 corresponds to the muscle loss portion of the implant site, facilitating regeneration of muscle tissue.

In certain embodiment, the biocompatible structure 90 can have three portions, one corresponds to a soft bone loss portion, one corresponds to a bard bone loss portion, and one corresponds to a muscle portion.

A variety of biocompatible structures 90 having one or more base structures can be produced according to the above example. In certain embodiments, the base structures can have different HAP/nanofiber/polymeric nanoparticle concentration in the polymer layer, where the HAP/nanofiber/polymeric nanoparticle concentration in the polymer film is closely related with the characters of the corresponding base structure. In certain embodiment, the base structures can have different polymer layer to polymer layer distance. In certain embodiment, the base structures can have different thickness of the bone particle layer or nanofiber/polymeric nanoparticle layer. In certain embodiment, the base structures can have different particle pore density. The HAP/nanofiber/polymeric nanoparticle concentration in the polymer film and the thickness and density of the particles in the particle layers are closely related with the characters of the produced biocompatible structure.

3D printing or additive manufacturing is a process of making a three-dimensional solid object of virtually any shape from a digital model. 3D printing is achieved using an additive process, where successive layers of material are laid down in different shapes. The material for manufacturing the biocompatible structure of the present disclosure includes polymers and particles, and the biocompatible structure is essentially a layered structure. Thus, in certain embodiments, the biocompatible structure of the present disclosure is suitable for 3D printing. In other embodiments, the biocompatible structure of the present disclosure is also suitable for layer by layer 2D printing In certain embodiment, a 3D model is built for an implant surgical site. The 3D model can be created with a computer aided design package or via 3D printer. The implant surgical site can be a bone and muscle surgical site that has bone and muscle tissue loss, a dental site that a crown is needed or a tooth need to be replaced, a tissue or a skin area that has tissue or skin loss, or any other implant surgical site of a patient that need an implant. The 3D model can be built based on 3D images such as x-ray computed tomography (CT) images, magnetic resonance imaging (MRI) images, or any other methods that can aid the construction of a 3D model. The 3D model can be constructed based on the shape, size, intensity, strength or other structure features of the surgical site directly, or the shape, size, intensity, strength or other structure features of a separated tissue such as a lost tooth, or the shape, size, intensity, strength or other structure features of a normal body portion that is symmetrical to the implant surgical site. In certain embodiments, a 3D structure model database is used to aid the construction of the 3D model of the implant surgical site. The 3D structure model database may be generated from 3D images collected from different patients or objects, and processed by a suitable algorithm. Once the 3D model is built for the implant surgical site or for the implant complementary to the implant surgical site, the implant can be generated by a 3D printer.

A 3D printer is a limited type of industrial robot that is capable of carrying out an additive process under computer control. A 3D printer from Stratasys Inc, Hewlett-Packard Company, 3D systems Corp., the ExOne Company, Voxeljet AG, Group Gorge, Camtek LTD., etc. can be used. In certain embodiment, a Solidoodle, a Cubify Cube, a Stratasys Mojo, a Hyrel E2 Hobbyist, or a customized RepRap 3D printer, or any other market available or lab built 3D printers can be used to generate the implant of the present disclosure.

The 3D printing technology is used for both prototyping and distributed manufacturing with applications in architecture, construction (AEC), industrial design, automotive, aerospace, military, engineering, civil engineering, dental and medical industries, biotech (human tissue replacement), fashion, footwear, jewelry, eyewear, education, geographic information systems, food, and many other fields. One study has found that open source 3D printing could become a mass market item because domestic 3D printers can offset their capital costs by enabling consumers to avoid costs associated with purchasing common household objects A large number of additive processes are now available. They differ in the way layers are deposited to create parts and in the materials that can be used. Some methods melt or soften material to produce the layers, e.g. selective laser melting (SLM) or direct metal laser sintering (DMLS), selective laser sintering (SLS), fused deposition modeling (FDM), while others cure liquid materials using different sophisticated technologies, e.g. stereolithography (SLA). With laminated object manufacturing (LOM), thin layers are cut to shape and joined together (e.g. paper, polymer, and metal). Each method has its own advantages and drawbacks, and some companies consequently offer a choice between powder and polymer for the material from which the object is built.

In certain embodiment of the present disclosure, the HAP particles, the bone particles, the polymer, the solution, or the polymer film can be used as material of a 3D printer to generate the implant including a layered structure.

In certain embodiment, the entire biocompatible structures are manufactured by 3D printing or layer by layer 2D printing, and used as the implant. In certain embodiment, the base structures formed from polymer strip layers and layers of tissue forming particle layers alternatively are produced by 3D printing or layer by layer 2D printing, and then assembled to generate the biocompatible structure. In certain embodiment, the polymer film is manufactured by 3D printing or layer by layer 2D printing, and then used to generate the base structures. In certain embodiment, a variety of cells, for example bone cells, stem cells, fibroblast cells, etc., can be seeded or printed on the biocompatible structure, the base structure, or the polymer film.

The biocompatible structure 90 can be any shape, size and weight to fit with an implant site. In certain embodiment, long bones were surgically removed from the tibia of goats, and biocompatible structures conform to the implant sited of the goats according to the present disclosure are used for bone regeneration of the goats.

In certain embodiment, when the biocompatible structure 90 having one base structure 100 is used in dental applications for bone generation, the concentration of HAP nanoparticles can be much higher than the concentration of HAP nanoparticles in the implant or the biocompatible structure for some other bone regeneration, for example, tibia regeneration. In certain embodiment, the biocompatible structure 90 for dental applications can be crumbled and forms a lot of particles with high surface area.

Figure 7A:
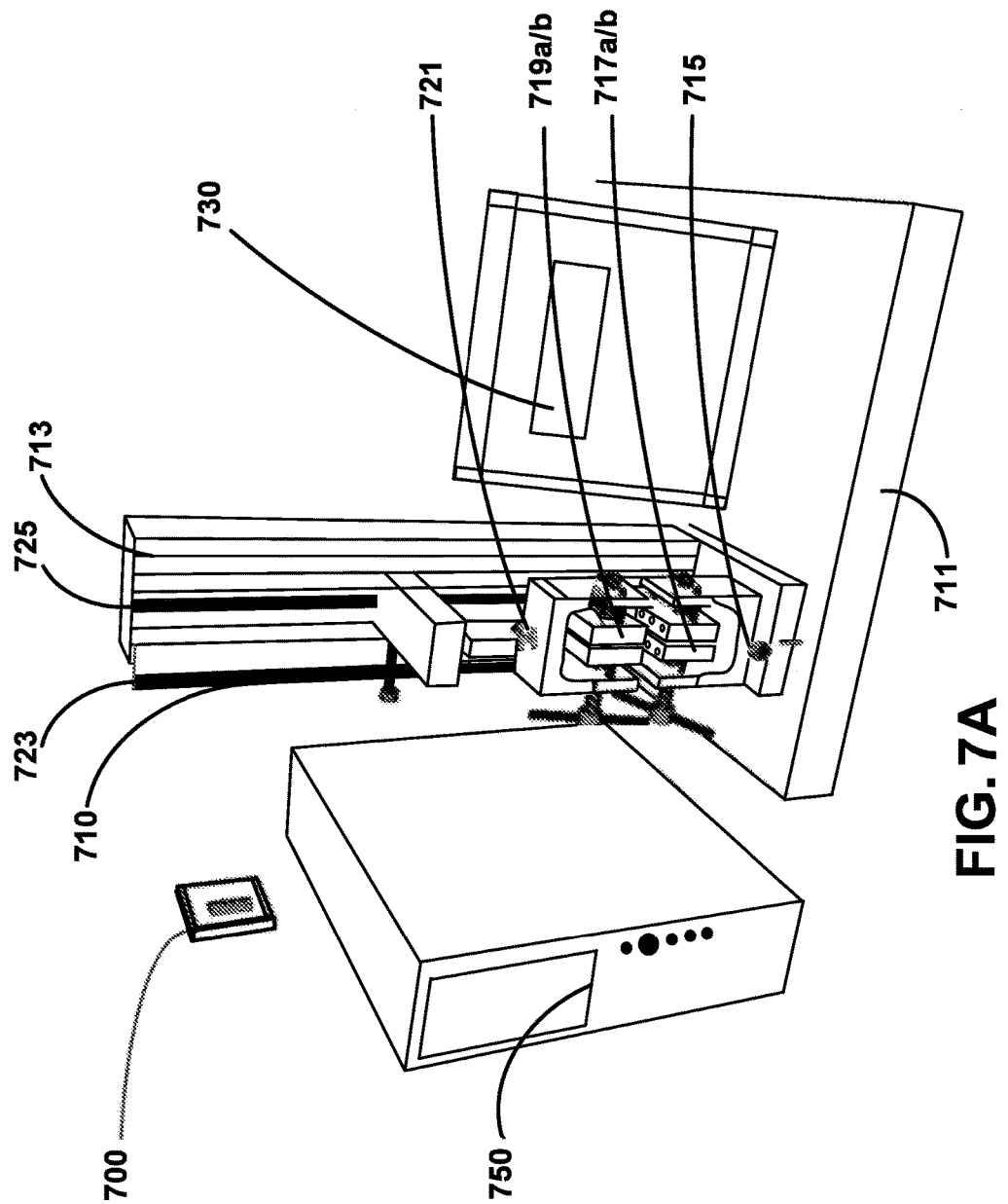
FIGS. 7A and 7B schematically show a pull test set up for measuring maximum load and maximum stress of polymer films according to certain embodiments of the present disclosure.
Figure 7B:
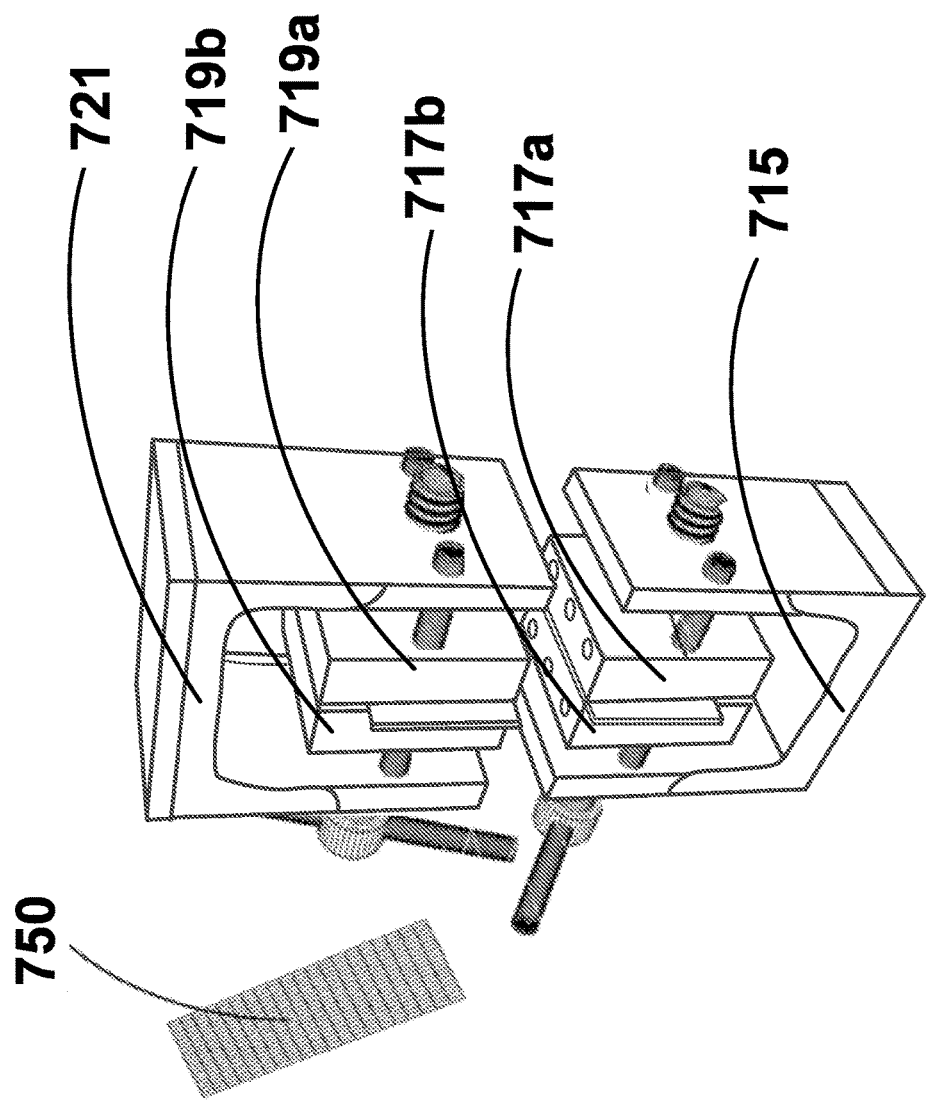

FIGS. 7A and 7B show a pull test system 700 used to measure the maximum load and maximum stress of polymer films 750 with various concentrations of polyurethane and HAP nanoparticle in accordance with certain embodiments of the present disclosure. In one example, the mechanical behavior of the composites was analyzed using an ADMET 7600 EXPERT single-column, universal, electromechanical testing machine. The instrument performs a "pull test" by stretching the polymer film in its axial direction and instantaneously produces a "csv" file using the eP2 Digital Controller and Gauge Safe Basic Testing Software. The pull test system 700 includes a pull test structure 710, a digital controller 730 and, optionally, a computer 750. The pull test structure 710 has a base 711, a column 713 fixed to and perpendicular to the base 711, a bottom head 715 connected with two bottom grips 717a and 717b facing each other, a top head 721 connected with two top grips 719a and 719b facing each other, a scale 723 attached to the column 713, and a rail 725 placed in the column 713. At least one of the top head 721 and the bottom head 715 is connected with the rail 725 and is movable along the rail 725. In this embodiment, the top head 721 is connected through a chain or a cable to a motor (not shown) and the chain or the cable pulls/drives the top head 721 along the rail 725. The top grips 719a/719b move together and at the same speed with the top head 721.

Polymer films 750 were prepared and tested. In certain embodiment, the polymer films 750 contain various concentrations of polyurethane and HAP nanoparticles. In one embodiment, the weight percentage of the HAP nanoparticles in the polymer films are 0%, 0.5%, 1%, 2%, 3%, 5%, 10%, 15%, 20% and 30% respectively. As described above, the weight percentage of the HAP nanoparticles is defined as the weight of the HAP nanoparticle powder (in gram) used for preparing the polymer film divided by the total weight of HAP nanoparticle powder (in gram) and solid polymers (in gram) used for preparing the polymer film 750. The polymer films 750 used in the test have predetermined dimensions. In certain embodiments, the size of the polymer films 750 is 6 cm×1.5 cm×0.02 cm. In certain embodiment, polymer films with the same concentration of HAP nanoparticles are prepared with different sizes for testing.

During the maximum load and maximum stress testing process, the top grips 721a/721b and the bottom grips 717a/717b clip two ends of the polymer film 750 in the longitudinal direction of the polymer film 750. The dimension of the polymer film 750 and the parameters of the force to be used are entered into the digital controller 730. In certain embodiments, the length of the polymer film used in the calculation is an effective length, for example, measured by the scale, from the bottom edges of the top grips 719a/719b to the top edges of the bottom grips 717a/717b. In certain embodiments, if the polymer film 750 clipped between the top grips 7191/b and the bottom grips 717a/b has a dog bone shape, the length used for calculation is the narrow portion of the dog bone shape. When the testing starts, the motor moves at least one of the top head 721 and the bottom head 715, for example, the top head 721. The top grips 719a/719b move together and at the same speed with the top head 721 to pull the polymer film 750 at a predetermined speed. In certain embodiment, the speed can be 0.01-2.5 mm per minute. The top grips 719a/719b move along the rail 725 at a predetermined speed to pull the polymer film 750 until the polymer film 750 breaks. The original dimensions of the polymer film 750, the moving speed of the top grips 719a/719b, the length of the polymer film 750 immediately before it breaks are recorded. The maximum load and the maximum stress are calculated. In certain embodiments, the calculation is performed by a processor (not shown) in the computer 750. The maximum load is the pull force (newton) applied to the polymer film 750 when the polymer film breaks. The maximum stress (KPa) is the pull force applied to the polymer film 750 when the polymer film 750 breaks divided by the cross-sectional area of the polymer film 750 (the original width times the original thickness of the polymer film 750).

The load and stress tests are performed for the polymer films 750 made according to the present disclosure. In certain embodiments, the polymer films contain various concentrations of polyurethane and HAP nanoparticles.

Figure 8:
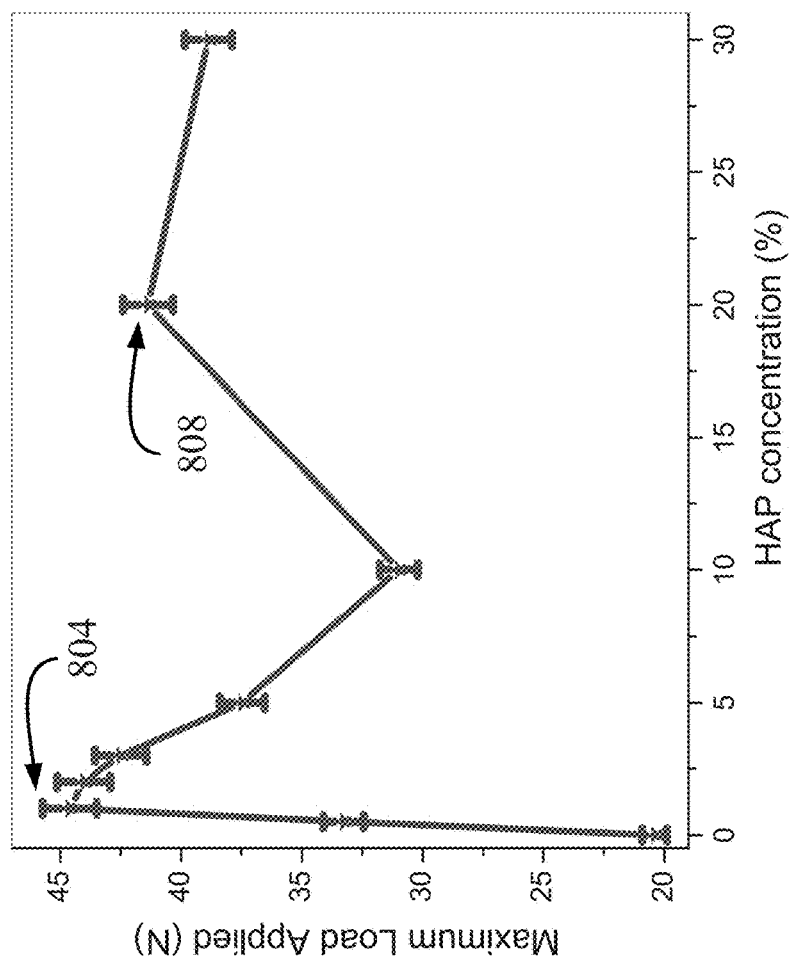
FIG. 8 schematically shows maximum load of the polymer films according to certain embodiments of the present disclosure.

FIG. 8 is a load graph of the polymer films 750 in a two dimensional coordinate system, which shows a functional relationship between the weight percentage of the HAP nanoparticles in a polymer film and a maximum load of that polymer film. The X-axis of the coordinate system is the weight percentage of the HAP nanoparticles and the Y-axis of the coordinate system is the maximum load of the polymer film. As shown in FIG. 8, the maximum load (in newton) for the polymer films 750 containing 0%, 0.5%, 1%, 2%, 3%, 5%, 10%, 20% and 30% of HAP nanoparticles are measured and calculated. The maximum load increases sharply from about 20 newton (N) to about 44 N when the HAP concentration increases from 0% to about 1%. Then the maximum load drops to about 31 N when the HAP concentration increases from 1% to around 10%. After that, the maximum load increases again to about 41 N at around 20% HAP concentration and drops to about 38 N at around 30% HAP concentration. Thus, the load graph has two peaks corresponding to 1% and around 20% of HAP concentration.

In certain embodiment, the second peak at around 20% HAP concentration in the load graph is named load peak.

Figure 9:
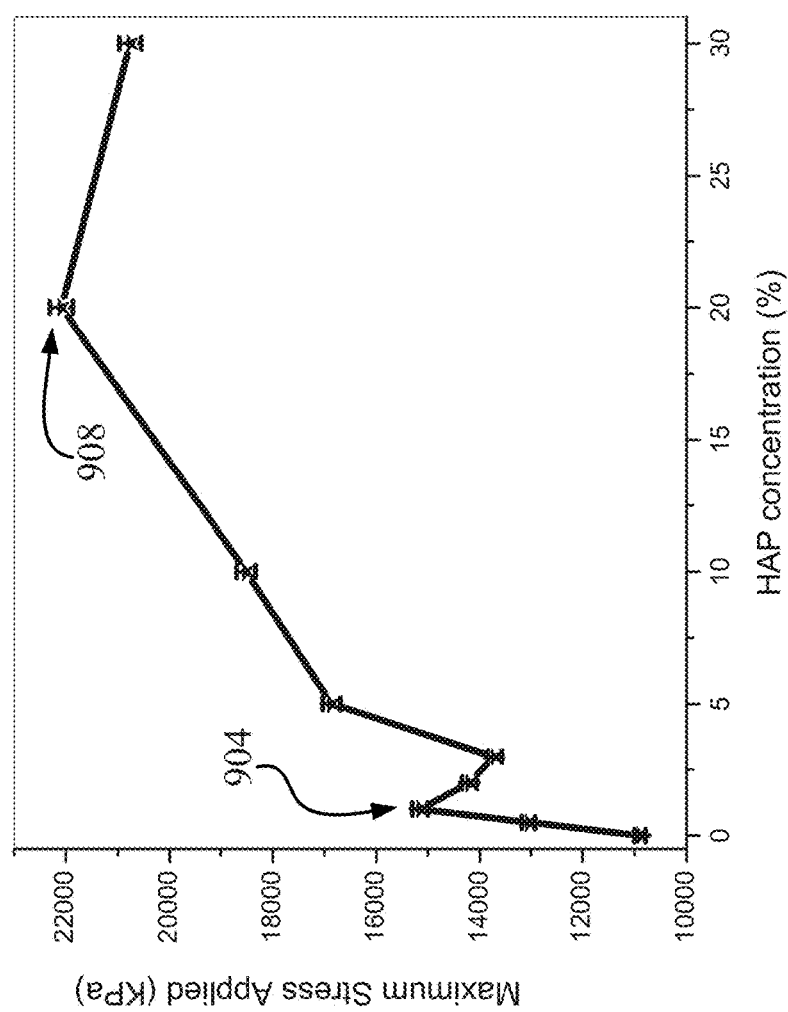
FIG. 9 schematically shows maximum stress of the polymer films according to certain embodiments of the present disclosure.

FIG. 9 is a stress graph of the polymer films 750 in a two dimensional coordinate system, which shows a functional relationship between the weight percentage of the HAP nanoparticles in a polymer film and a maximum load of that polymer film. The X-axis of the coordinate system is the weight percentage of the HAP nanoparticles and the Y-axis of the coordinate system is the maximum stress of the polymer film 550. As shown in FIG. 9, the maximum stress (in KPa) for the polymer films containing 0%, 0.5%, 1%, 2%, 3%, 5%, 10%, 20% and 30% of HAP nanoparticles are measured and calculated. The maximum stress increases from about 11,000 KPa to about 15,000 KPa when the HAP concentration increases from 0% to about 1%. Then the maximum stress decreases to about 13,600 KPa when the HAP concentration increases from 1% to about 3%. After that, the maximum stress increases to about 22,000 KPa when the HAP concentration increases from about 3% to about 20%. Further increasing HAP concentration in the polymer films from about 20% to 30% can result in decreasing of the maximum stress from 22,000 to about 20,800 KPa. Thus, the stress graph has two peaks corresponding to 1% and 20% of HAP concentration. In certain embodiment, the second peak at 20% HAP concentration in the stress graph is named stress peak.

In certain embodiments, a computer 750 can be used to calculate optimal weight percentage of HAP in the polymer film 750 according to the above load and stress graphs of a series of polymer films 750. The computer 750, utilizing one or more CPUs, can receive the data from the pull test structure 710 and the digital controller 730, run a calculation software, and then present the result on a monitor.

An optimal weigh percentage of HAP in the polymer film 750 is determined based on the results from the load graph and the stress graph by the computer 730. In certain embodiments, both the load graph and the stress graph have at least two peaks. The first peak 804 in the load graph corresponding to a lower HAP concentration, and the second peak 808 in the load graph corresponding to a higher HAP concentration. The first peak 904 in the stress graph corresponding to a lower HAP concentration, and the second peak 908 in the stress graph corresponding to a higher HAP concentration. The second peak 808 in the load graph is named load peak 808, and the second peak 908 in the stress graph is named stress peak 908. The peak values from the load peak 808 and the stress peak 908 are extracted. In this example, both of the load peak 808 and the stress peak 908 correspond to a HAP weight percentage (HAP concentration) of 20%. The maximum value and the minimum value of the load peak 808 and the stress peak 708 are determined. In this example, both the maximum value and the minimum value are 20%. The optimal concentration range has an upper limit value and a lower limit value. The upper limit value is the maximum value plus a first predetermined value. The lower limit value is the minimum value minus a second predetermined value. Each of the first predetermined value and the second predetermined value can be, for example, 10%, 5%, or 0%. Accordingly, in this example, the optimal concentration range of the HAP in the polymer film is 10%-30%, preferably 15%-25%, and more preferably 20%.

In another example, the load peak 808 and the stress peak 908 have different values. For example, the load peak may be at 17.5% and the stress peak may be at 22.5%. Accordingly, the maximum value is 22.5% and the minimum value is 17.5%. With the first and second predetermined values at about 10%, preferably 5%, and more preferably 0%, the optimal concentration ranges of the HAP weight percentage in the polymer film are 7.5%-32.5%, preferably 12.5%-27.5%, and more preferably 17.5%-22.5%. In other embodiments, the first and second predetermined values can be different values.

In certain embodiments, according to the results shown in FIGS. 8 and 9, the polymer film with 20% HAP concentration shows good structure stability and strength.

In certain embodiments, the biocompatible structure 90 including one base structure 100 prepared according to the present disclosure for the treatment of animals and/or humans. In certain embodiment, long bones were surgically removed from the tibia of goats. For generating long bones of these goats, biocompatible structures of a weight about 1.0-2.5 grams (g) were used. For example, 10 implants with the weight of 2.39 g, 2.34 g, 2.11 g, 1.86 g, 2.135 g, 2.18 g, 1.55 g, 2.5 g, 1.22 g, and 1.69 g, respectively, were used to generate long bones for the goats with surgically removed tibia part. For the above 10 examples, the biocompatible structure was made by using 4.52 g of polymer (polyurethane), 0.45 g of HAP nanoparticles, and 15 g of bone particles.

The bone growth using the implant having one or more the biocompatible structures 100 according to embodiments of the present disclosure has maturity and integrity.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A biocompatible structure comprising,
    a first base structure, comprising:
        a plurality of first polymer layers stacked to have a predetermined shape, wherein each of the plurality of first polymer layers comprises a first polymer and first tissue forming nanoparticles, and a first weight percentage of the first tissue forming nanoparticles to the first polymer is in a range of about 0.5-95%; and
        a plurality of first spacer layers disposed between each of two neighboring first polymer layers of the plurality of first polymer layers, wherein the plurality of first spacer layers comprises first spacer particles;
    a second base structure disposed on the first base structure, comprising:
        a plurality of second polymer layers stacked to have a predetermined shape, wherein each of the plurality of second polymer layers comprises a second polymer and a second tissue forming nanoparticles, a second weight percentage of the second tissue forming nanoparticles to the second polymer is in a range of about 0.5-95%, and the first weight percentage is greater than the second weight percentage; and
        a plurality of second spacer particle layers disposed between each of two neighboring second polymer layers of the plurality of second polymer layers, wherein the plurality of second spacer particle layers comprises second spacer particles;
    a coating surrounding the first base structure and the second base structure; and
    a plurality of third spacer particles attached to an outer surface of the coating.

2. The biocompatible structure of claim 1, wherein the first polymer is the same as the second polymer, the first tissue forming nanoparticles are HAP nanoparticles, the second tissue forming nanoparticles are nanofibers, the first weight percentage is about 15-30%, and the second weight percentage is about 10-25%.

3. The biocompatible structure of claim 1, wherein the first polymer is the same as the second polymer, the first tissue forming nanoparticles are the same as the second tissue forming nanoparticles, the first spacer particles and the second spacer particles are the same as the plurality of third spacer particles, the first weight percentage is about 15-30%, and the second weight percentage is about 10-25%.

4. The biocompatible structure of claim 3, wherein the first weight percentage is about 17-23%, and the second weight percentage is about 15-20%.

5. The biocompatible structure of claim 4, wherein the first weight percentage is about 20%, and the second weight percentage is about 18%.

6. The biocompatible structure of claim 1, wherein at least one of a thickness of each first polymer layer of the plurality of first polymer layers, a distance between two neighboring first polymer layers of the plurality of first polymer layers, a thickness of each first spacer layer of the plurality of first spacer layers, a porosity of the first spacer particles is different from a thickness of each second polymer layer of the plurality of second polymer layers, a distance between two neighboring second polymer layers of the plurality of second polymer layers, a thickness of each second spacer layer of the plurality of second spacer layers, a porosity of the second spacer particles, respectively, such that when being applied to an implant site, each of the first base structure and the second base structure corresponds to a tissue in the implant site, and aids regeneration of the corresponding tissue.

7. The biocompatible structure claim 6, wherein the distance between two neighboring first polymer layers of the plurality of first polymer layers is greater than the distance between two neighboring second polymer layers of the plurality of second polymer layers.

8. The biocompatible structure claim 6, wherein the density of the first spacer particles in the plurality of first spacer layers is greater than the density of the second spacer particles in the plurality of second spacer layers.

9. The biocompatible structure claim 6, wherein a degradation rate of the first base structure is slower than a degradation rate of the second base structure.

10. The biocompatible structure claim 6, wherein each of the first base structure and the second base structure of the biocompatible structure has a size and shape conforming to a size and shape of the corresponding tissue of the implant site.

11. The biocompatible structure of claim 1,
    wherein each of the first polymer and the second polymer comprises a synthetic biodegradable polymer, a biodegradable polymer derived from natural source, or a mixture thereof;
        wherein the synthetic biodegradable polymer comprises polyurethanes, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(desaminotyrosinetyrosylhexyl ester iminocarbonate) (poly(DTH iminocarbonate)), poly(bisphenol A iminocarbonate), poly(ortho ester), polycyanoacrylate, polyphosphazene, or a mixture thereof; and
wherein the biodegradable polymer derived from natural source comprises polysaccharides, proteins, or a mixture thereof;
wherein each of the first and second tissue forming nanoparticles comprises nanoparticles of hydroxypatites (HAP), tricalcium phosphates, mixed calcium phosphates and calcium carbonate, bone particles of zenograft, bone particles of allografts, bone particles of autografts, bone particles of alloplastic grafts, polymeric nanoparticles, nanofibers, or a mixture thereof; and
wherein each of the first spacer particles, the second spacer particles, and the plurality of third spacer particles comprises nano-sized bone particles, micro-sized bone particles, polymeric nanoparticles, nanofibers, or a mixture thereof.

12. The biocompatible structure of claim 1, wherein the first spacer particles are bone particles, and the second spacer particles are polymeric nanoparticles or polymeric nanofibers.

13. The biocompatible structure of claim 1, further comprising a third tissue forming material,
wherein the third tissue forming material comprises a bioactive material, cells, or a mixture thereof;
wherein the bioactive material comprises proteins, enzymes, growth factors, amino acids, bone morphogenic proteins, platelet derived growth factors, vascular endothelial growth factors, or a mixture thereof; and
wherein the cells comprise epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof.

14. The biocompatible structure of claim 1, wherein at least one of the plurality of first polymer layers and the plurality of second polymer layers has a length of about 0.05-200 centimeter, a width of about 0.02-50 centimeter, and a thickness of about 0.01-500 millimeter, and wherein each of the first base structure and the second base structure has a cylindrical shape, rectangular shape, or a spherical shape cylindrical shape, rectangular shape or a spherical shape.

* * * * *